United States Patent [19]
Dickinson et al.

[11] Patent Number: 5,567,884
[45] Date of Patent: Oct. 22, 1996

[54] CIRCUIT BOARD ASSEMBLY TORSION TESTER AND METHOD

[75] Inventors: Gerard T. Dickinson, Owego, N.Y.; James L. McGinniss, Jr., Friendsville, Pa.; Ronald F. Tokarz, Maine, N.Y.; Aleksander Zubelewicz, Binghamton, N.Y.

[73] Assignee: International Business Machines Corporation, Armonk, N.Y.

[21] Appl. No.: 208,774

[22] Filed: Mar. 9, 1994

[51] Int. Cl.⁶ .................................................. G01N 3/20
[52] U.S. Cl. .................. 73/814; 73/810; 73/847; 73/848
[58] Field of Search ............................ 73/849, 851, 853, 73/814, 847, 848, 810; 324/158 F

[56] References Cited

U.S. PATENT DOCUMENTS

| | | |
|---|---|---|
| 3,381,526 | 5/1968 | Rastogi et al. . |
| 3,665,751 | 5/1972 | Paine et al. ............................... 73/766 |
| 4,003,247 | 1/1977 | Moser et al. .............................. 73/814 |
| 4,567,774 | 2/1986 | Manahan et al. . |
| 4,895,027 | 1/1990 | Manahan, Sr. . |
| 4,958,522 | 9/1990 | McKinlay . |
| 5,079,955 | 1/1992 | Eberhardt . |
| 5,184,517 | 2/1993 | Kelzer ....................................... 73/851 |
| 5,195,384 | 3/1993 | Duesler, Jr. et al. ................... 73/865.6 |

FOREIGN PATENT DOCUMENTS

| | | |
|---|---|---|
| 1723679 | 3/1990 | U.S.S.R. . |

OTHER PUBLICATIONS

ITL SM Tech Feb. 1985, "SMC Card Torque Tester", by Center et al (Unpublished).
Document No. 9402–019, "Mechanical Deflection System Reference Manual", pp. 1–29, by Zubelewicz et al (Unpublished).
Document No. 9402–027, "Mechanical Deflection System Test Methodolgy", pp. 1–16, by Zubelewicz (Unpublished).

*Primary Examiner*—R. Raevis
*Attorney, Agent, or Firm*—Michael E. Belk

[57] ABSTRACT

A torsion tester for circuit board assemblies (boards) clamps opposite edges of the board and cyclicly twists the board to provide substantially pure sheer stress in interconnection joints to SMT components for replicating failure modes due to thermal cycling. The boards are automatically centered in the clamps, the distance between the clamps is automatically measured, and the machine rotates one of the clamps to produce out-of-plane deflection which repeat within 0.01 degree per inch of the distance to provide repeatable results. During testing the maximum deflection and torque of each cycle and the location and cycle count at each failure is automatically recorded until a large population of failures is obtained. The population of failures is automatically compared to a statistical database of previous populations to identify any unusual deviations and for determining the reliability of the production process. The system can be used either to monitor the quality of existing board assembly line, to determine the affect or quality of a change in a board assembly process, or to determine the reliability or quality of a new board assembly process.

40 Claims, 21 Drawing Sheets

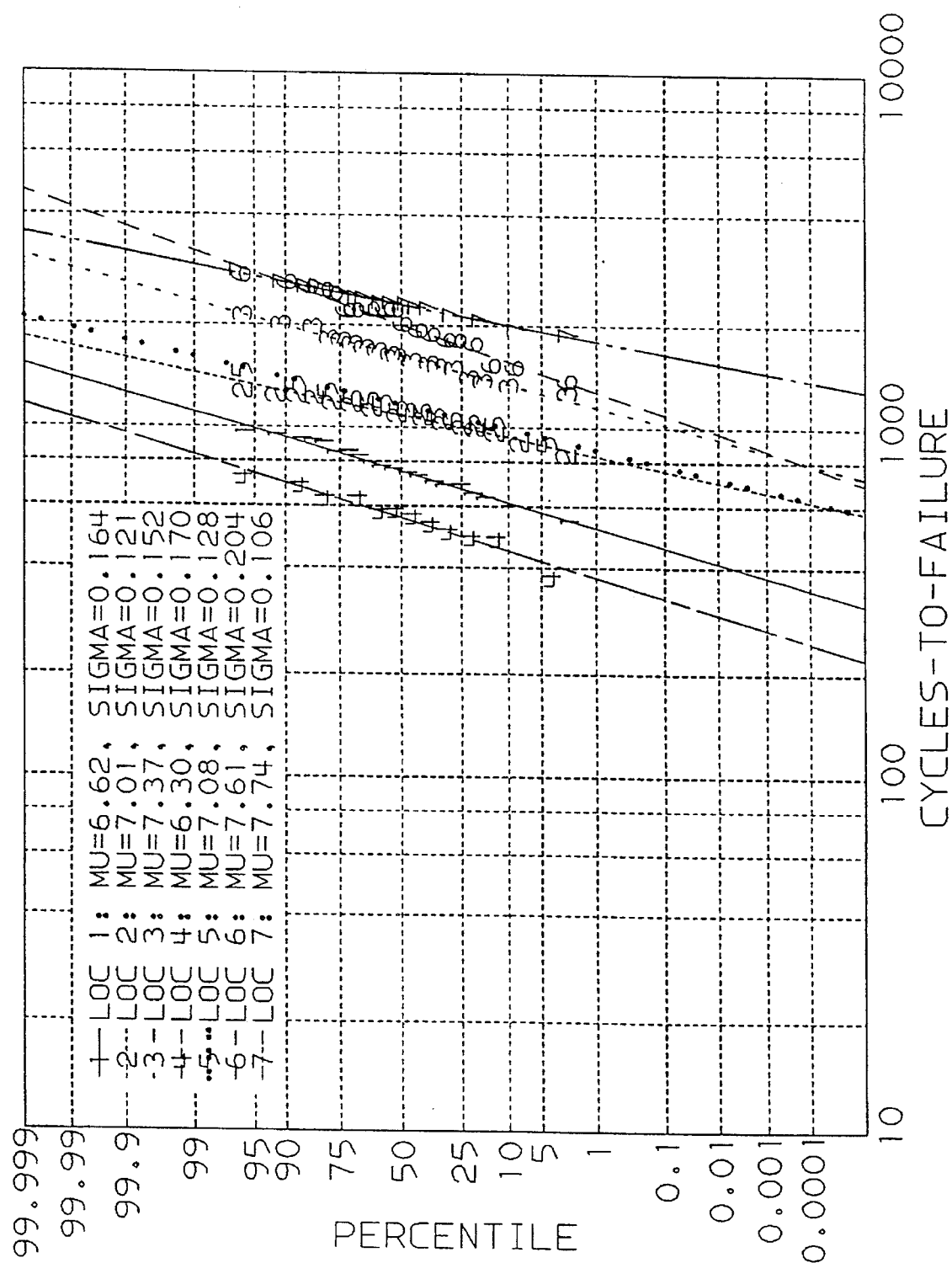

| | MDS MEAN LIFE, $N_{50}$ | STANDARD DEVIATION, SIGMA |
|---|---|---|
| REWORK | 797 | 0.771 |
| STANDARD | 1183 | 0.152 |
| LEAD-ON-CHIP | 2677 | 0.183 |

FIG. 12

CIRCUIT BOARD ASSEMBLY TORSION TESTER AND METHOD

FIELD OF INVENTION

This invention is related to methods and apparatus to evaluate the quality of surface mount technology (SMT) electronic assembly processes for circuit board assembly process quality control and/or for optimizing circuit board assembly processes. More specifically, the invention is related to destructive testing of SMT circuit board assemblies for predicting the reliability of SMT solder joints when exposed to thermal fatigue during operation.

BACKGROUND

Solder joints are a critical element of surface mount attachment of electronic components. Previously, continuous process quality of SMT circuit board assembly was monitored using visual inspection, pull tests, and periodic Accelerated Thermal Cycling (ATC). Visual inspection is not sufficient because many defects are not visually observable. For example, joints of grid array surface mount components can not be readily observed. In pull testing, assembled components are pulled off the circuit board and the appearance of the fractured joints indicate the quality of the assembly process. Again, this method does not disclose all the defects because it does not replicate field failure mechanisms. Both visual inspection and pull testing require the services of a skilled operator for extensive periods of time for each board assembly tested. ATC is a good method of finding defects which could cause field failures Also, ATC testing can be automated so a skilled operator is only required to electrically test the board after cycling. However, ATC is not a practical testing method for monitoring continuous process quality because the total test time is too long. Typically, ATC data is not available until weeks after production.

Cyclic bending has been used to test the quality of soldered joints in circuit board assemblies. Japanese Patent JP 03-245600 discloses "a test device to check a printed board in soldering quality." The test uses "a probe after the printed circuit board is subjected to a prescribed frequency of bending tests." In Soviet Union patent SU 1723679-A1 constant bending upward and downward is applied to a PCB for "non-destructive quality control testing of metalizations and contact junctions."

Cyclic bending fatigue testing has also been used in other fields for determining bulk fatigue properties of many materials. For example U.S. Pat. No. 3,381,526 to Rastogi et al discloses a method and machine to perform such fatigue tests on cantilever beams with a waist section. Manahan et al in U.S. Pat. No. 4,567,774 discloses "a miniaturized bend test of specimens" and the mechanical behavior of the material is determined from the measurement taken during the "bending of the specimen and is processed according to the principles of linear or non-linear material mechanics;" and in U.S. Pat. No. 4,895,027 discloses a method for determining "plane strain fracture toughness, dynamic plane strain crack initiation and arrest fracture toughness" and other fracture characteristics. U.S. Pat. No. 5,184,517 to Kelzer discloses a "test fixture and test method is designed to establish statistical information concerning the breaking force for deflection of a printed circuit board when the print circuit board is broken along pre-existing score lines." U.S. Pat. No. 5,079,955 to Eberhardt discloses "A fatigue testing system subjects a test specimen to a rotary stress applied about an axis at one or both ends which is perpendicular to the axis of the test selected specimen" and is used to detect "stress failure" for tested materials.

Torsional testing has also been used to evaluate mechanical properties of materials and structures. In U.S. Pat. No. 4,958,522 McKinlay discloses a sample "is held between two axially aligned jaws. . . The sample is subjected to a twisting force by rotation of one of the jaws and the force and angle of deflection are measured. This gives a relative determination of the board's structural property and is used to assess damage to the corrugated medium during corrugation and subsequent processing steps such as printing."

All the above citations are hereby incorporated by reference to provide an enabling disclosure and to support the claims to which applicant is entitled by law.

OBJECTS OF THE INVENTION

The following are some of the objects of this invention.

To develop a method of continuous control of circuit board assembly soldering processes to maintain the quality of solder joint fatigue life.

To provide a measurement of solder joint fatigue life which is closely related to joint fatigue life in actual use.

To provide a method of simulating field fatigue conditions in a test which can be performed sufficiently quick for practical application in process control.

To provide a method of evaluating the failure of soldered joints during simulation tests to determine the quality of joint fatigue life during actual field use.

SUMMARY OF THE INVENTION

The invention of Applicants is a system which includes a testing process and a novel machine for using the process. The system can be used to monitor assembly process quality or to determine the reliability of newly developed assembly processes. The system is known as the Mechanical Deflection System (MDS). The MDS machine includes a torsion tester which imposes controlled repeatable sheer stress to the board and components mounted thereon. The stress produced by the machine is similar to that imposed on components due to thermal cycling of the assembly during field use. The torsion tester includes self-centering fixturing to assure that the circuit board is held in a repeatable position and twisted about the central longitudinal axis of the board. The fixtures include one stationary clamp and one rotating clamp which is connected to a backlash free motor and servo system. The distance between the clamps can be adjusted to fit various board sizes. The clamps have slips to automatically control the maximum clamping force to prevent board damage resulting in spurious results.

The machine also includes a computer, connected to regulate the motor, and which has apparatus to control the motor for precisely applying either a desired twist angle or a desired torque during the cyclic twisting of the board. An optical meter measures the angle of twist and a torque meter measures the torque applied to the fixturing. The meters generate signals and are connected to transmit the signals to the computer. The circuit board is also connected to the computer to allow electrical resistance of critical joints to be monitored during testing to determine the occurrence of failures. The computer includes apparatus to determine the cycle count at which each failure occurs and the location of the failure. The machine has a data base in which the location and cycle count at which each failure occurs is recorded. The test is continued until a large number of failures is produced. The data base also includes failure cycle and location data for a base process. The base process could be another process for making similar boards or the same process at previous times. The failure cycles and locations of boards produced by a target process are compared to failure cycles and locations of boards produced by the base process. The comparison between the failure locations and cycles are analyzed to statistically determine the reliability of the joints.

Other objects, features and advantages of the invention will be apparent from the detailed description of the invention and the following drawings.

BRIEF DESCRIPTION OF THE DRAWINGS

FIG. 9 is a plot of MDS fatigue results in terms of distribution of fails for each location in the example process of the invention.

FIG. 12 shows a summary of the conclusions of the MDS test of FIG. 9.

DETAILED DESCRIPTION OF THE INVENTION

Figure 1:
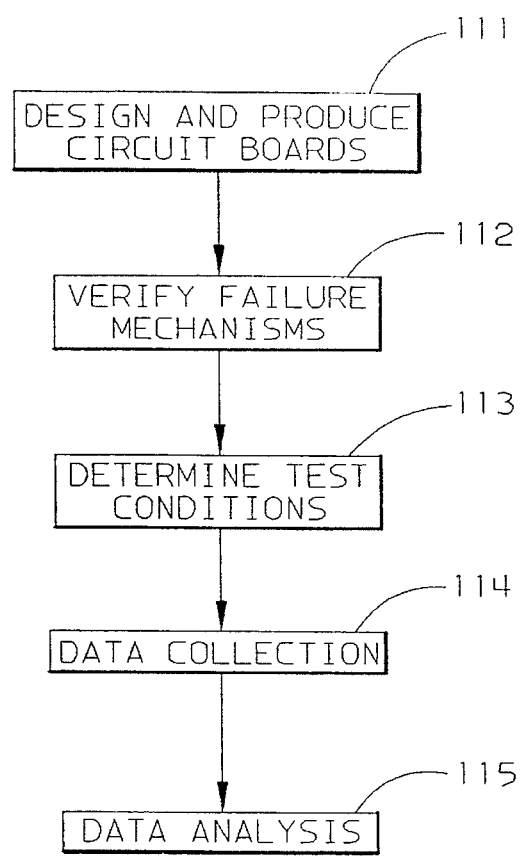
FIG. 1 is a process flow diagram for the overall method of a specific embodiment of the invention.

The process of the invention replicates ATC failure mechanisms in a very accelerated manner. The machine of the invention imposes cyclic out-of-plane deformation to an assembled printed circuit board. A portion of the deformation is transferred to SMT solder joints in proportion to the stiffness of the board, rigidity of the electronic components, and compliance of leads and the solder interconnects themselves. The stress magnitude in solder joints is also a function of the component location on the board, the component type, the position of the joint relative to the component, and component to components interactions. The out-of-plane deformation leads to a complex stress system within each individual joint. The methodology disclosed herein was developed through extensive modeling and testing to properly interpret the quality of the assembly. This description will enable those skilled in the art to define the proper test parameters to use the process and equipment described for quick and accurate assembly process quality verification and/or assembly process optimization. MDS testing can be conducted in a number of different ways, and the those skilled in the art may develop their own approach. However, it is preferred that the logical path illustrated in FIG. 1 be maintained. In FIG. 1, step 111 the circuit boards used for testing are designed, debugged, tested, and produced. The test of this invention may be carried out using product assemblies selected from those normally produced on the target process, but preferably, custom designed test assemblies, which are periodically assembled in the same target process as the product assemblies, are used. The test assemblies would mimic the functional product assemblies but provide for automatic generation of failure data. Alternately, both approaches may be used in combination. For example, special test cards may be used to develop and optimize an assembly process and to produce an experience base, and then actual production cards can be tested and analyzed for continuous process quality control.

MDS testing applies various degrees of stresses to solder joints, depending on component type, component location, and joint position. One can reduce the variation by properly selecting the board and component layout. The preferred ratio of the board length to width is approximately one to two. The shorter ends of the board should be placed in the tester fixture. Complex board geometry might also be considered, but this may require design of a special fixture.

Figure 2:
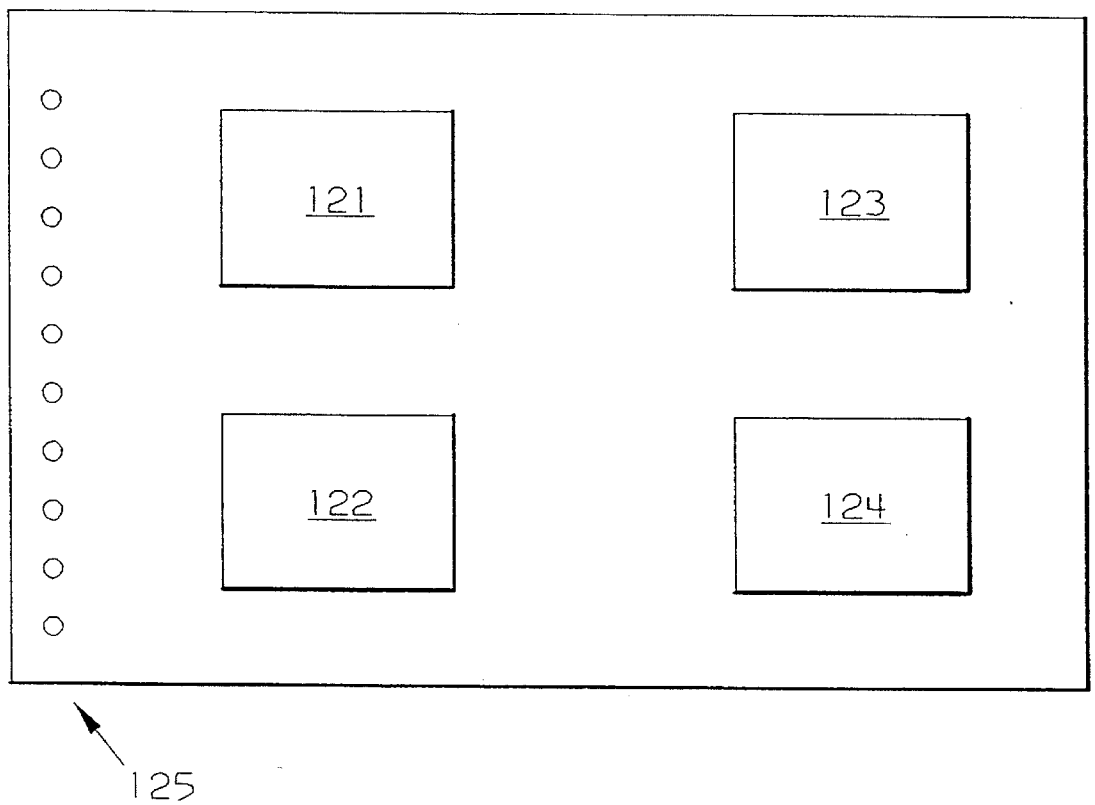
FIG. 2 is an embodiment of the circuit board of the invention showing components mounted symetrically along the two axis of the board.

As shown in FIG. 2, in the cards used for testing, preferrably component locations such as 121, 122, 123, and 124 should be symmetrical with respect to the board axes. Symmetry increases the effective number of data points per board, e.g. if four components are placed symmetrically on a board, then each of the components will experience the same stress in the MDS test, and therefore four equivalent readings will be received from a single board. The proper layout of the components can significantly reduce the number of boards that require testing.

The MDS tester operates at high frequencies (as high a 0.1 Hertz) to achieve a high cycle count in a relatively short time. Visual or periodic electrical assessment can be performed by pausing the test. Preferably, the boards being tested should provide for automatic detection of failures such as connectors for test signals. Preferably, any such connectors should be subject to minimum stress during MDS testing. Therefore, it is recommended that the connectors are parallel to the clamped edges of the card and near the narrow edge of the board which will be inserted in the fixed clamp as shown at 125.

In step 112, failure mechanisms are verified. MDS test results are valid only if the failure mechanisms produced in MDS testing are the same as the failure mechanisms which are produced under the product operating conditions (proper failure mechanisms). Usually the information on failure mechanisms for commonly used technologies is available in industry technical publications. Preferably, potential failure mechanisms are identified and understood prior to running the MDS test. The MDS fracture mechanisms need verification through construction analysis and/or visual joints assessment.

Although the MDS test was developed to replicate joint failure mechanisms, MDS torsion cycles do not exactly mimic product "duty" cycles; therefore, it is possible that the MDS test may not reflect all the factors needed for proper product evaluation, i.e. local thermal mismatches, creep of organic materials. For these reasons failure mechanisms must be verified for proper use of MDS testing.

In step 113, the test conditions are determined. When defining MDS test conditions, two factors are important—first, proper failure mechanisms should be achieved in the minimum test time, and second the amount of data gathered during testing must be sufficient to guarantee adequate assessment of the assembly process. Critical test conditions are the angle of twist, the cycle frequency, and data frequency during testing.

Although testing may be executed using torque control, it is preferrable to use deformation (angle of twist) control. Solder joints receive stress in proportion to the board deformation, therefore the angle of twist is the primary variable that controls the stress magnitude. Also, as the circuit board substrate is fatigued during the test the torque may vary in relation to the angle of twist. The angle of twist is preferably selected between 0.4 degrees and 1.2 degrees per inch of effective length. The effective length of the card is the distance between the MDS clamps. In general, leaded components can be tested at a higher range of deformation (preferably up to 0.9 degrees per inch of length), while leadless components such as Ball Grid Array technology require lower deformation (preferably from 0.4 to 0.6 degrees per inch). Selection of the proper angle of twist is critical. Over-stressed components may exhibit undesired mechanisms of failure, e.g. high lead-tin solders may develop transgranular instead of commonly observed intergranular failure. For example, field failure reports or, ATC testing of Ball Grid Array (BGA) components mounted on a particular circuit board may indicates that the only expected failure mechanism in operation is separation of the balls from the pads. However, during MDS setup debugging, the pads and lines separate from the board surface. In such a case the angle of twist should be reduced or the speed of cycling reduced until the identified failure mechanism is obtained. After proper test setup is obtained, such separation may indicate weaknesses of the board design or the assembly process.

As a general rule, the MDS should be conducted at the highest frequency which would allow for replication of the proper assembly failure mechanisms. The typical range of frequencies is in between 0.05 to 0.15 Hz and preferrably should not exceed 0.5 Hz.

In all cases, the MDS test conditions need verification before board testing commences to assure that the proper failure mechanisms are achieved in the minimum time on test. Note that the cycle counts per component type and per component location may vary. Some components may fail at very early stages of cycling, while others may experience very long fatigue life. Therefore, MDS test conditions should be optimized in order to provide meaningful information for all assembly processes. Preferably the mean number of cycles should be:

1,000 Cycles< Recommended Mean Life<20,000 Cycles.

The lower cycle limit assures the correct high fatigue mode of metallurgical failure, while the upper one has a strictly practical meaning, which is that the MDS test duration should not be longer than necessary. In order to predict the optimum test conditions, one can use the following equations;

$$\Phi_{desired} = \Phi_{pre\text{-}test} \left[ \frac{N_{desired}}{N_{pre\text{-}test}} \right]^r$$

where the factor r may vary between 0.3 and 0.4. In most cases, one can assume that the factor r=⅓. Furthermore, $N_{pre\text{-}test}$ and $N_{desired}$ are the pre-test and desired cycles to failure respectively. Also, $\Phi_{pre\text{-}test}$ and $\Phi_{desired}$ are the appropriate angles of twist applied to the assembled boards.

Preferably, the first "main" run, after the MDS test conditions are determined, is used to re-verify the MDS test setup.

Figure 3:
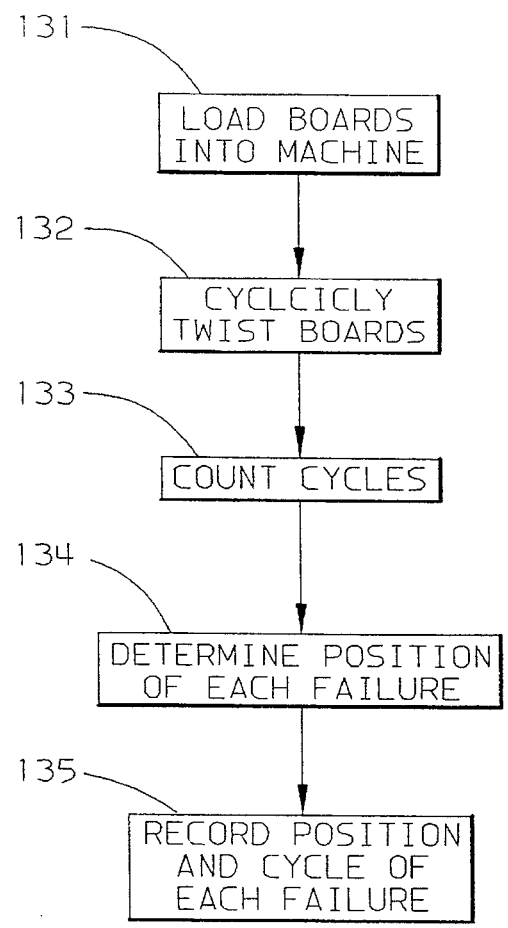
FIG. 3 is a process flow diagram showing a specific embodiment of the process for testing and collecting data of the invention.

In step 114, data are collected during MDS testing. In accordance with the verified test procedure as shown in step 131 of FIG. 3, the card is clamped into the MDS test machine, and in step 132 is twisted at predetermined twist angles at predetermined frequencies for a predetermined number of cycles. In step 133, the number of cycles is counted during the test, and in step 134, the position of each detected failure is determined. In step 135, for each such failure, the cycle number and failure position (the specific joint) is recorded for later analysis. Preferably, the circuit card is connected to a computer system in order to automatically count cycles, determine failure locations, and log each failure with associated cycle count and location in a data base for later statistical analysis performed on the same computer system. If this is not possible, the electrical reading or visual assessments must be gathered at a sufficient frequency during the test in order to provide meaningful statistical analysis.

In step 115 the joint failure data gathered during testing are analyzed. The most critical element of the MDS test methodology is the analysis of the joint failure data collected during testing. The factors that influence the joint fatigue life during testing are as follows:
technology type, (TSOP, BGA, PLCC, . . .);
board flexural stiffness;
component and the interconnect compliances;

component location on the tested board;
component to components interactions.

Each of these factors alters the joint fatigue life during MDS testing. This requires a special algorithm for data analysis of MDS test results.

Figure 4:
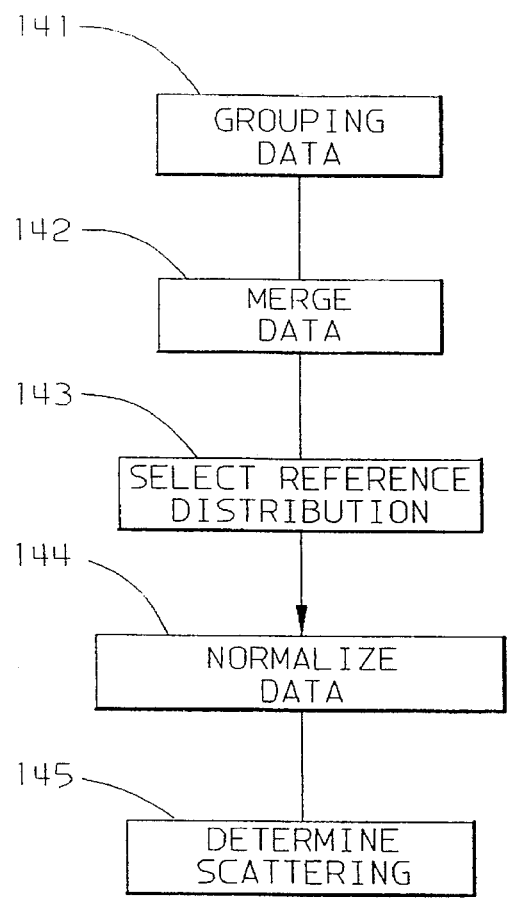
FIG. 4 is a process flow diagram showing a specific embodiment of the steps of the statistical analysis of the invention.

FIG. 4 shows the steps for performing the statistical analysis of the invention. In step 141, fatigue data is grouped according to component type, joint location within the tested components, and location of the component on the tested board. The MDS test should provide enough data to build a fails distribution for each selected variable. In step 142 we attempt to merge data. Some of the distributions can be merged together, especially those which belong to the same technology. It is especially convenient if components of the same technology occupy positions which are symmetrical with respect to the axis about which the circuit board is twisted. Since the stress may vary from joint to joint, the fatigue life will vary as well.

Distributions of fails are characterized by the mean cyclic life and the scattering of the data. Thus, the individual distributions of fails can be normalized to some reference. In step 143 a reference distribution is selected for such normalization. Although there is no a special rule for selecting the reference distribution, we prefer to choose a distribution which locates itself in between other distributions. In step 144, the mean lives of the distribution of fails is compared to the selected reference distribuiton, preferrably, the correlation factors are calculated as follows:

$$CF_i = \frac{(N_{50})_{reference}}{(N_{50})_i}.$$

Each individual cycle count within the i-th distribution is multiplied by the correlation factor $CF_i$. Then, the corrected cycle counts are equivalent to those in the reference distribution. Once all the individual distributions are normalized and merged to the referenced one, all the fatigue data can be used to build the equivalent distribution (scattering) of fails in step. 145. The equivalent distribution of fails characterizes the quality of the solder joints under consideration.

MDS testing can be used for two basic applications. First MDS can be used as a self-learning monitor of assembly process quality. Second MDS can be used in combination with ATC testing to assess the reliability of new technologies. The scattering of fails and the mean fatigue life define the quality of an assembly process. The scattering of fails alone might provide a sufficient quality measure for assembly processes monitoring. However, development of new technologies require an understanding of the mean fatigue life expectancy of the assembly. In such a case, ATC testing can be conducted in parallel with MDS test in order to verify failure mechanisms and establish bridge between ATC and MDS cycles.

Figure 5:
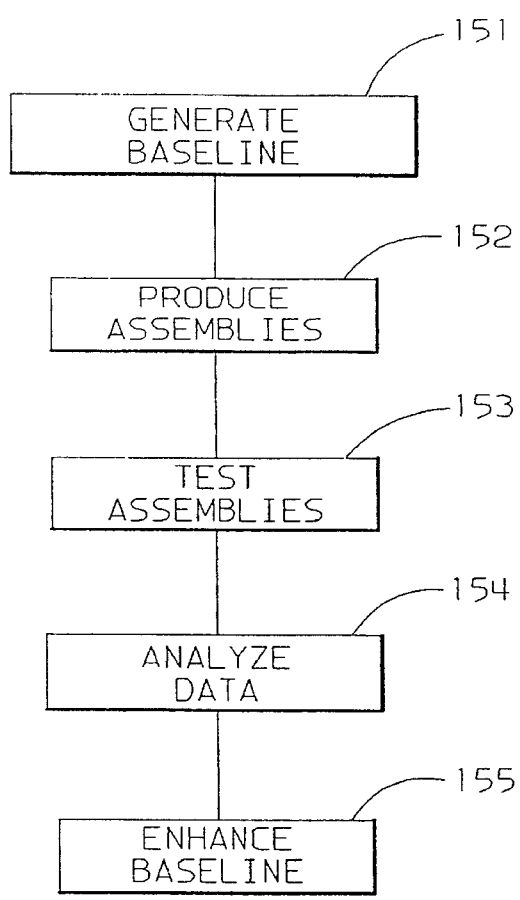
FIG. 5 is a process flow diagram showing the steps of using the MDS system as a monitor of assembly processes.

FIG. 5 illustrates the process of using the MDS system as a monitor of assembly processes. In this mode the MDS system is designed to expose the development of assembly process defects and allows for very fast corrective actions.

In step 151, A baseline reference distribution is generated from the mean MDS life and the fails scattering (distribution) per component type and per component location resulting from previous MDS tests for the same assembly process. Only statistically valid MDS fatigue data gathered for the assembly process during high quality production is used for the baseline. In step 152, test vehicles must be produced in the assembly line or the functional boards must be selected from those normally produced on the assembly line with a frequency which would allow for proper quality control of the line.

In step 153, the assemblies are tested in accordance with verified test procedures previously discussed. In step 154 the data is analyzed as described above in reference to FIG. 4. The baseline established in step 151 is used as a reference distribution. Any observed anomalies (e.g., life shorter than expected unexpected failure mechanisms etc.) would indicate the presence of flaws in the assembly process. In some cases, MDS testing was found more sensitive than ATC testing in detecting assembly defects (such as module tilt, mis-registration, etc.). Since MDS test duration is measured in hours, this test is considered as a "near" real time monitor of an assembly line.

The MDS monitor is a self-learning method, by which statistical data gathered periodically and over a long period of time can enhance baseline data and allow for better understanding of the process critical variables. In this way, MDS test methodology can optimize assembly processes. In step 155, if there are no anomalies, then the current fails distribution can be combined into the baseline. Alternately if anomalies are identified and process flaws are identified which correlate to the anomalies then the current test can be used to predict specific process flaws from test results. For example, if investigation of an anomalies fails distribution discloses that pads have begun separating from the circuit board during testing, and investigation determines that the cause of pad separation is a contaminated seeding solution, then similar anomalies in fail distributions will immediately indicate that the seeding solution should be checked for contamination. As a first example, the MDS test method was used to analyze the quality of a TSOP assembly processes. The analysis included three parts: quality of the TSOP assembly process for standard components, quality of the rework process for standard components, and quality of a process for lead-on-chip type of components. In this example, the scattering of cycles to failure provides the basis for the analysis.

As a first step 111 of FIG. 1, a test vehicle was designed and

Figure 6:
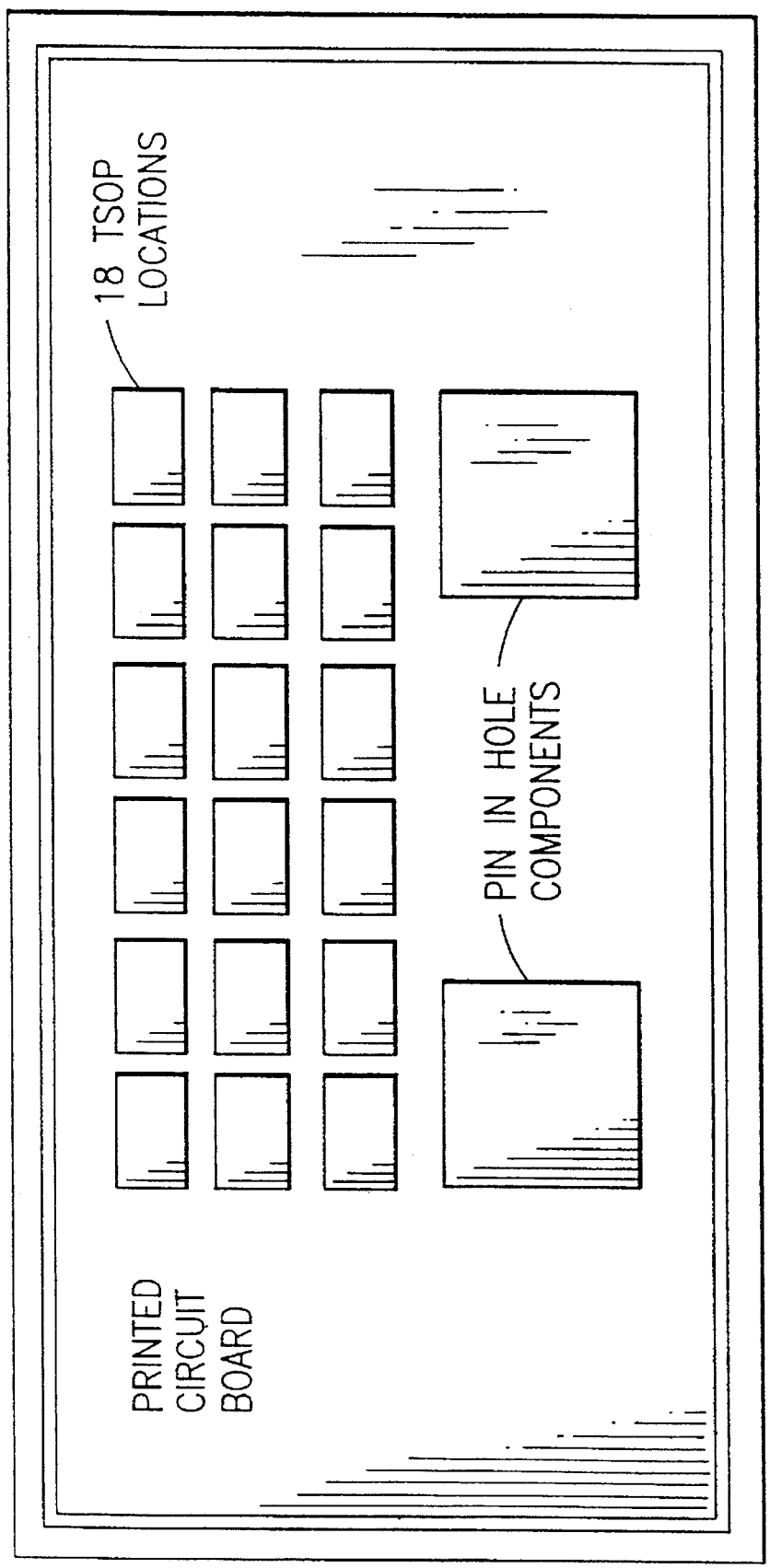
FIG. 6 shows 18 TSOP components assembled to a specific embodiment of the test circuit board of the invention, symmetrically about one axis.
Figure 7B:
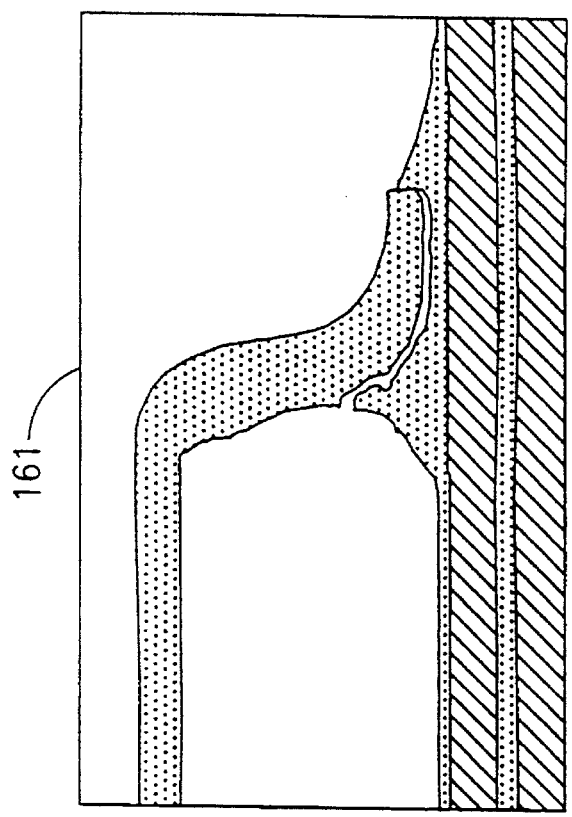
FIG. 7 shows the leads of lead-on-chip and standard TSOPs attached by a propriety process.
Figure 7A:
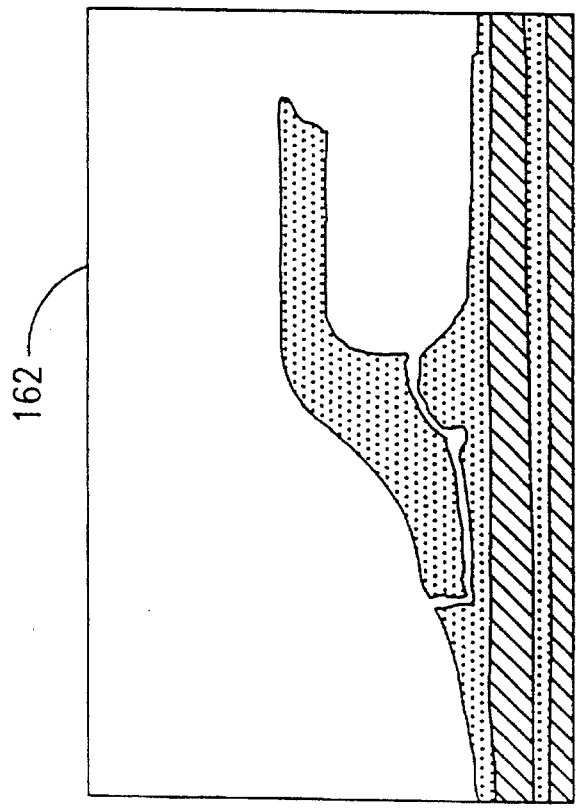

The TSOP components were assembled to the test vehicle as shown in FIG. 6. The vehicle is a double sided board with 18 TSOP components on each side. The components are placed symmetrically on the board (mirror image of the components with respect to the length of the board as shown on FIG. 6). Both sides are identical. As a result, there are four components in every equivalent location. Each component has all the solder joints stitched (serially connected) together to simplify design and production, so that the MDS fails were counted on a component basis. Eight boards were produced for this test. Boards 1 and 6 have reworked components placed in the locations 4 and 5. Boards 4, 5, and 6 have assembled lead-on-chip components on the top side at all nine locations. The back side of the boards have assembled standard TSOP components. As shown in FIG. 7 lead-on-chip TSOP's 161 have longer and more compliant leads compared with standard TSOP's 162.

The second step 112 of FIG. 1 is to verify the failure mechanisms.

Figure 8A:
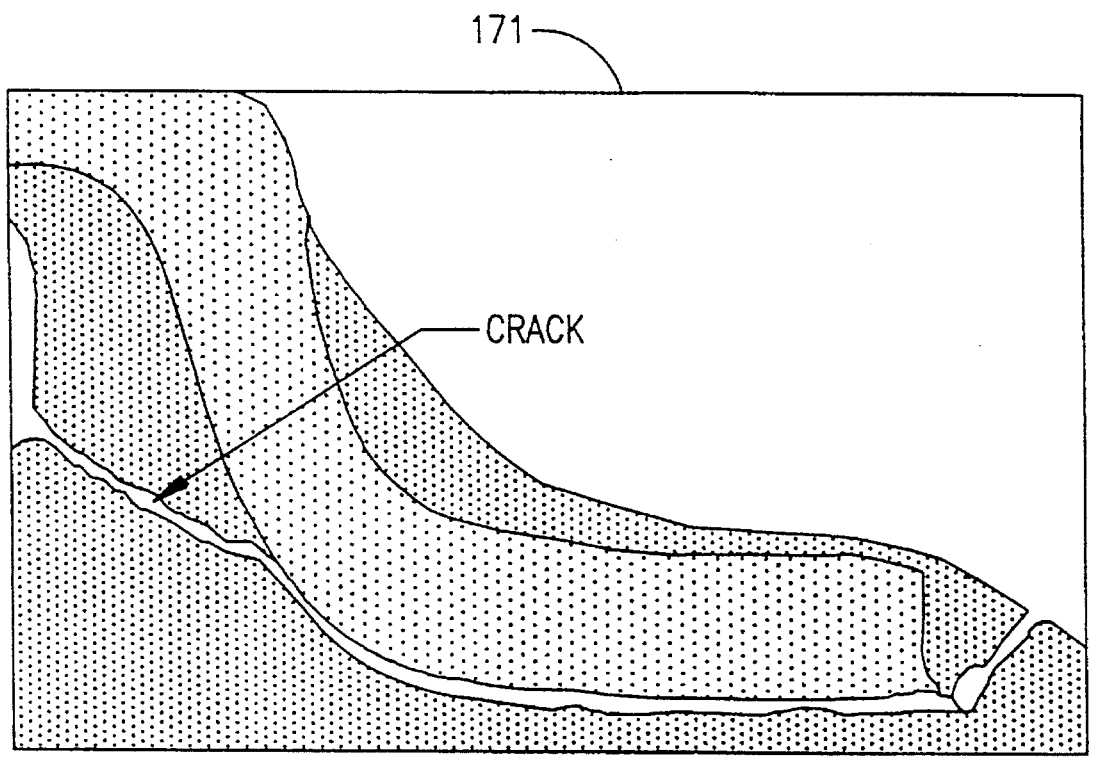
FIG. 8 illustrates ATC and MDS testing failures in an example of the process of the invention.
Figure 8B:
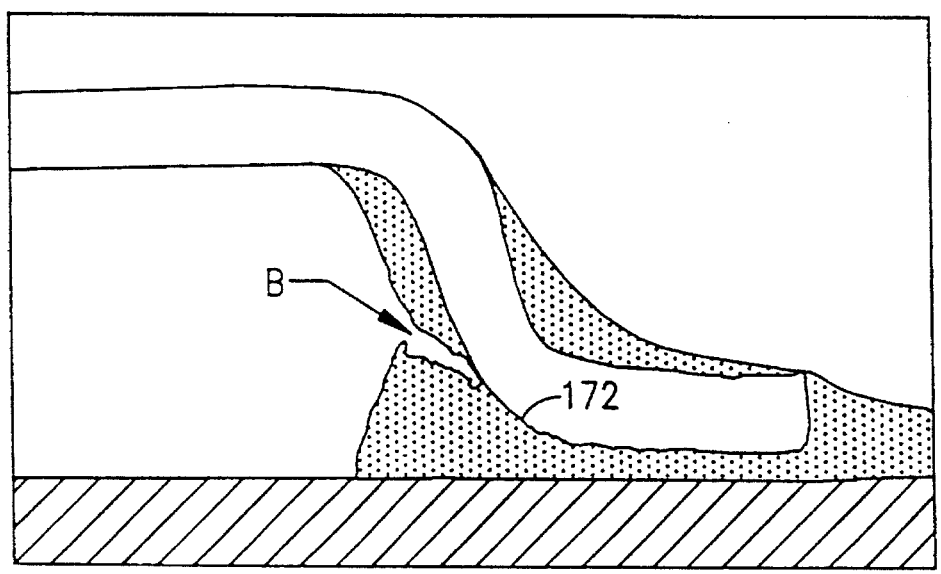
Figure 10:
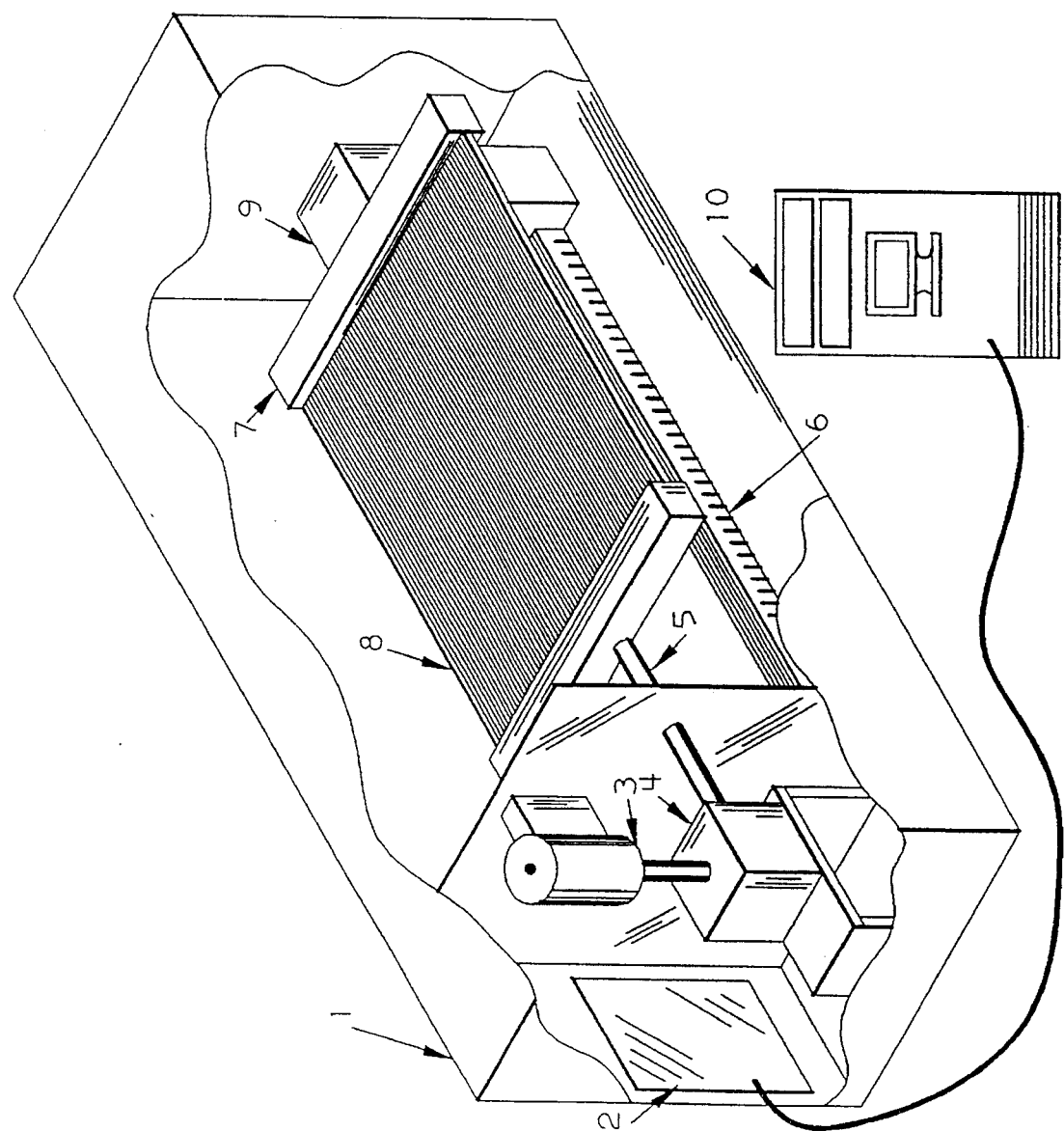
FIG. 10 illustrates an embodiment of an MDS tester of the invention.

MDS fracture mechanisms must resemble the mechanisms received from ATC testing. Such comparison were made for TSOP solder joints and it was concluded that the mechanisms are indeed the same. FIG. 8 shows ATC testing failure 171 and MDS testing failure 172 for comparison.

The third step 113 of FIG. 1, test conditions are determined.

Initially, a single setup card was used to identify proper test conditions. The angle of twist was set at 0.9 degrees per inch of the card length. The results indicated that the test could be conducted at higher stress levels for reducing the excessive cycle count to failure. Therefore, the angle of twist was set at 1.2 degrees per inch of the effective card length.

The fourth step 114 of FIG. 1, is data collection. Torsion testing commenced and fatigue data were gathered for the first seven equivalent locations. FIG. 9 describes the MDS fatigue results in terms of distribution of fails for each location. The number of fails at locations 8 and 9 was insufficient to build a statistically valid distributions of fails. Note that these distributions are very similar. The distributions can be bridged together to a reference location. In this case, location no. 5 was chosen for that purpose. Subsequently, mean fatigue lives from locations 1, 2, 3, 4, 6, and 7 were compared to the mean life from location number 5. The correlation factors $CF_1$ through $CF_7$ ($CF_i$ was defined above) were used to re-scale the cycle counts from each location. The resulting total number of data points per location number 5 was;

standard components—112, reworked components—12, lead-on-chip components—30.

Figure 11:
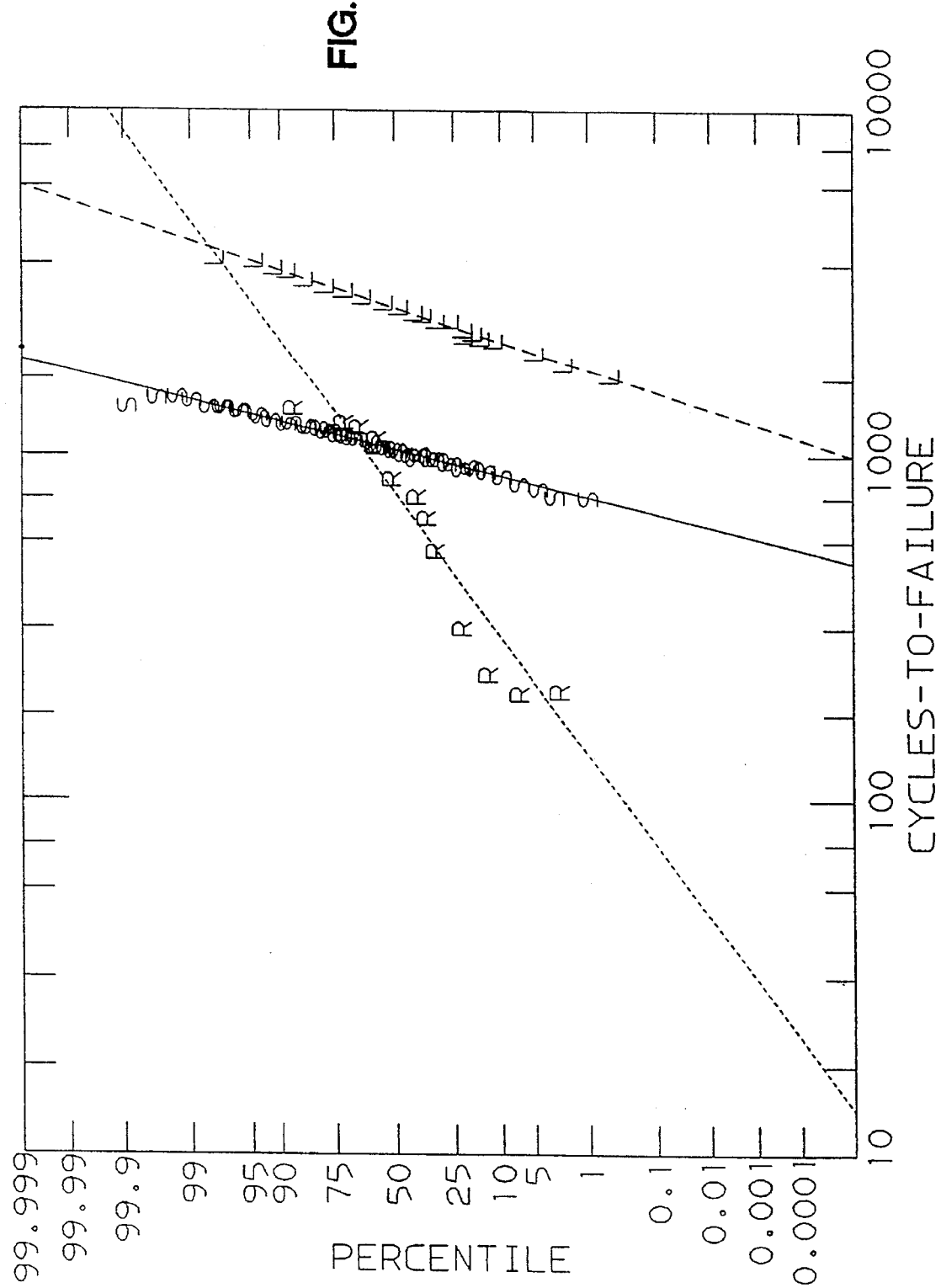
FIG. 11 is a plot of the final distribution of failures in the example of FIG. 9.

The final distributions of fails are presented on FIG. 11, and the conclusions from the test are summarized in FIG. 12.

As a second example, the MDS test method was used to analyze the reliability of a new process to attach chip carrier modules (components) to circuit boards (test vehicles) using a matrix of solder balls herein called Ball Grid Array (BGA).

Figure 13A:
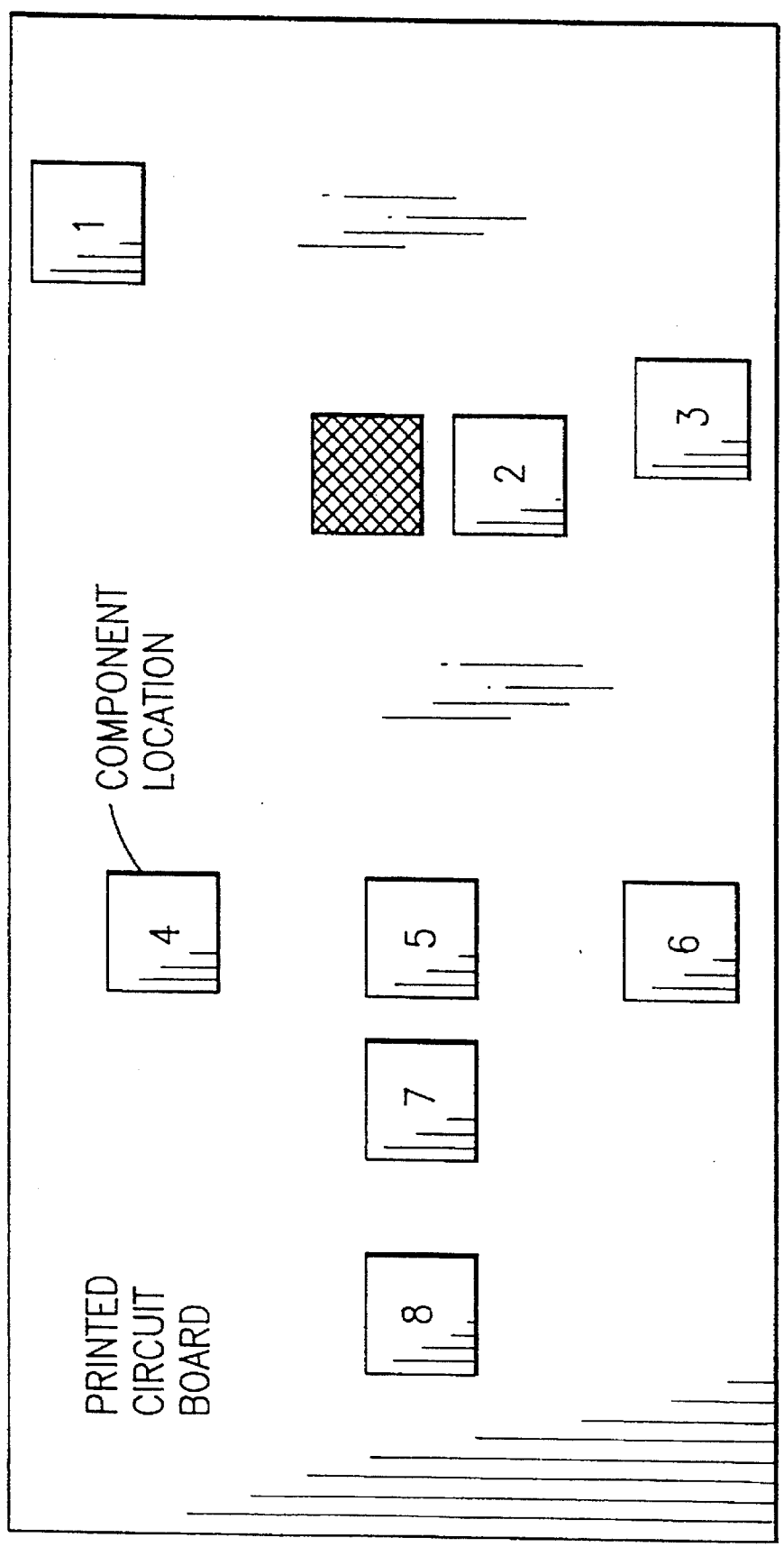
FIG. 13a illustrates another non-symmetrical test vehicle embodiment used in an example embodiment of the MDS process.

As shown in the first step 111 of FIG. 1, test vehicles are designed and produced. Eight BGA components were assembled to a test vehicle, as shown on FIG. 13a. Electrical readings were recorded for each component. There is no symmetry in locations of the components, so that the count of cycles to failure varied from component to component.

Figure 13C:
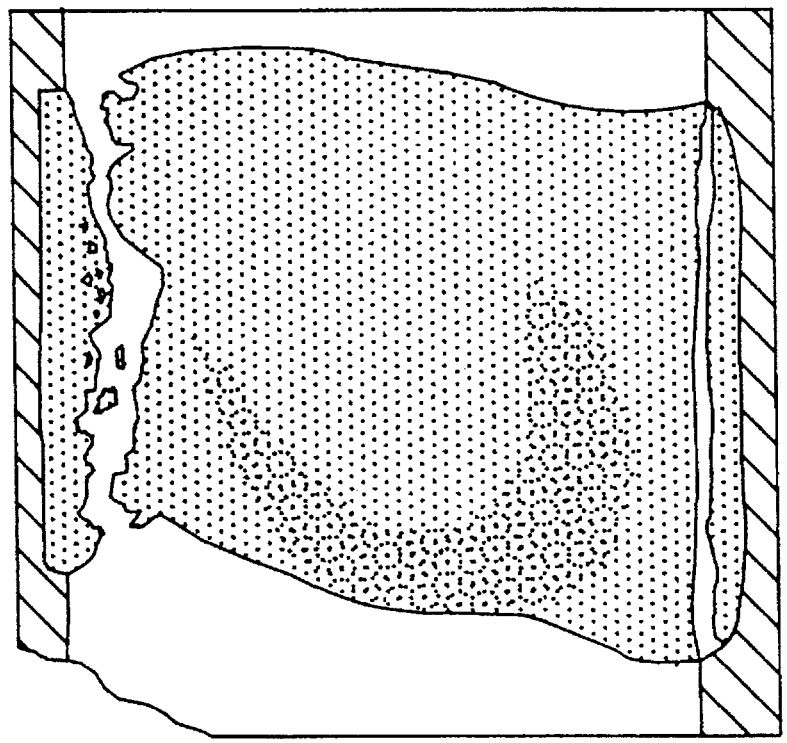
FIG. 13c illustrates a failure produced by MDS testing at a location corresponding to that in 13b, showing a similar failure mechanism.
Figure 13B:
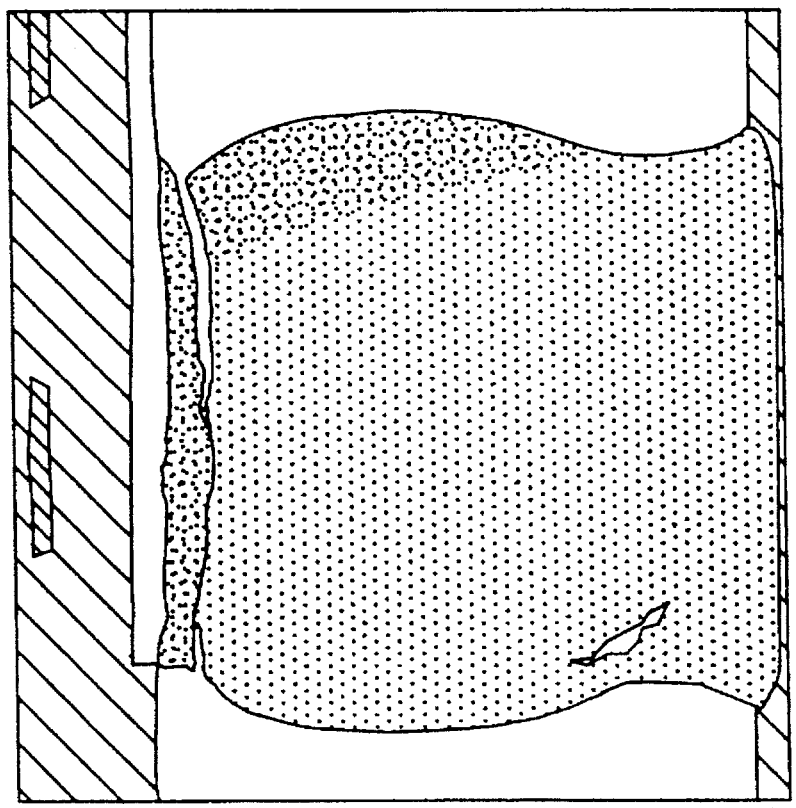
FIG. 13b shows a failure produced by ATC testing.

As shown in the second step 112 of FIG. 2, failure mechanisms were verified. Normally only one ATC test should be required, but in order to verify the MDS test method statistically, fifteen boards were cycled between the temperatures of 20 and 80 degrees C. with a frequency of 0.00083 Hz to generate multiple failures on the boards. MDS tests were run on three boards using 0.45, 0.6 and 0.9 degrees per inch of the board length and 0.1 HZ frequency. 0.9 degrees per inch caused partial separation of copper pads from tested boards which is not a valid mechanism since the ATC tested boards did not fail by that mechanism. Comparison of ATC testing as shown in FIG. 13b with MDS failures at 0.6 degrees per inch as shown in FIG. 13c shows that failure mechanisms are similar.

As shown in the third step 113 of FIG. 1, test procedures were determined. The first test runs indicated that both 0.6 and 0.45 degrees per inch were satisfactory in terms of failure mechanisms; however, the time required for testing at 0.45 degrees per inch was excessive, thus 0.6 inches per inch of board length was selected for further tests. In the forth step 114 of FIG. 1, data was collected for an additional 12 cards using the predetermined test proceedure and failure data (the cycle and location of each failure) was collected.

Figure 14:
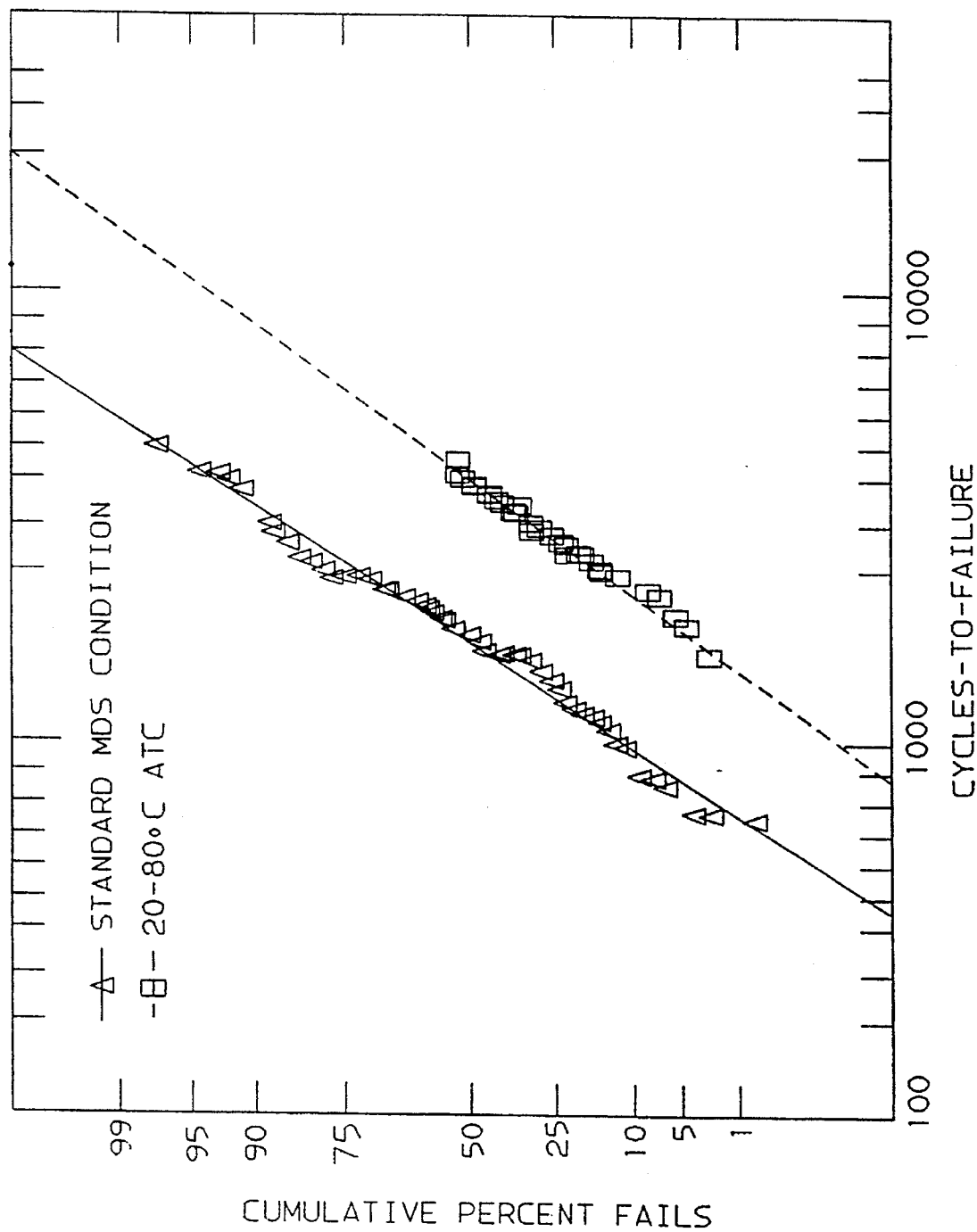
FIG. 14 is a plot of the normalized distribution of ATC and MDS testing fails.

The final step 115 in FIG. 1 is statistical analysis of data. The normalized distributions of fails were plotted for MDS and ATC test conditions in FIG. 14. The individual distributions of fails were normalized using Finite Element Analysis and predictive fatigue models. The normalized MDS and ATC plots look almost identical. The only difference is in the test duration. The ATC test would require more than half a year to achieve 100 percent failed components, while the MDS test needed only 16 hours to generate a complete distribution of fails.

The MDS testing methodology requires highly accurate repeatable test parameters. The novel combination of features provided in the MDS torsion test machine provides the accuracy and repeatability required and automatic features for convenience and to prevent errors during testing.

Figure 15:
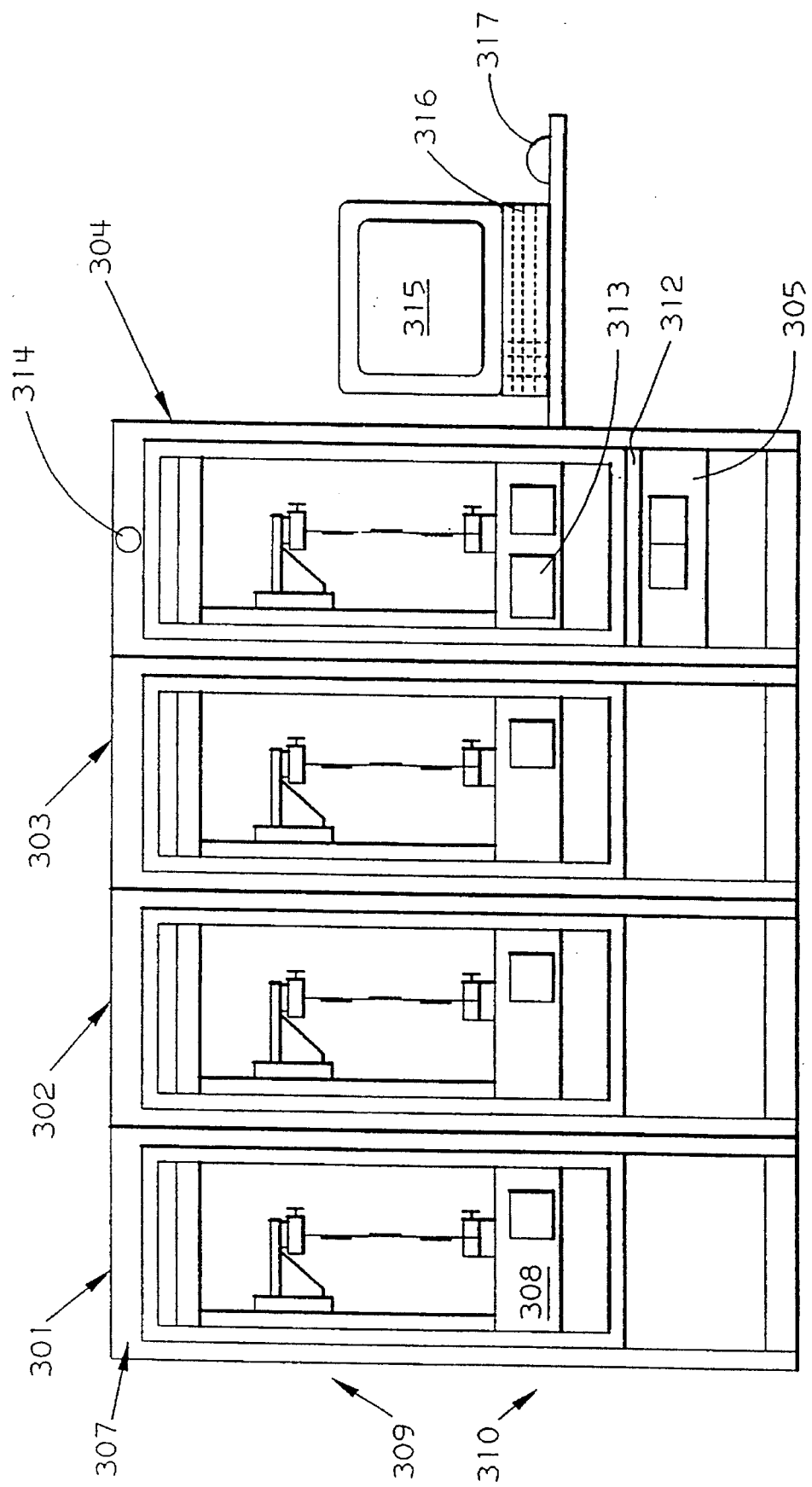
FIG. 15 shows another embodiment of the MDS tester of the invention, including four rest stations.

As shown schematically in FIG. 15, the MDS machine is an assembly of 1 to 4 torsion testing stations 301–304 interconnected with a computer 305 such as an IBM PS/2 7537 (PS/2 is a trade mark of IBM). The test stations each include an industry standard 19 inch rack enclosure 307, an operator panel 308, an upper test section 309 and a lower equipment section 310. Each machine contains a main station 304 in which is mounted the computer and a test circuit monitoring control box 312. The operator panel of the main station contains the power control 313. A big red emergency power off (EPO) button is provided at the top of the main station. The EPO is connected to disconnect all power from every station upon activation. The enclosures may be bolted together as shown to form a unitary machine. A display 315, keyboard 316 and mouse 317 provide the primary user-interface with the computer.

Figure 16:
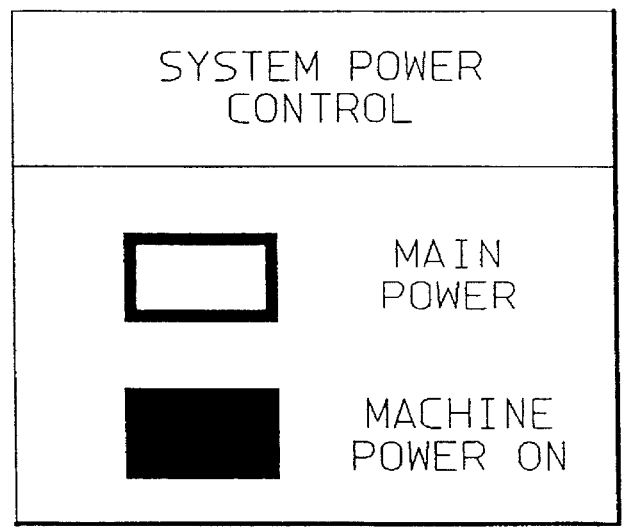
FIG. 16 is an expanded view of the power control area of the operator's panel of the tester of FIG. 15.

FIG. 16 shows an expanded view of power control 313 (see FIG. 16) of the operator's panel for the main station. The power control includes a startup switch 320 (labeled "Machine Power On"), and a power on button 321 (labeled "MAIN POWER").

Figure 17:
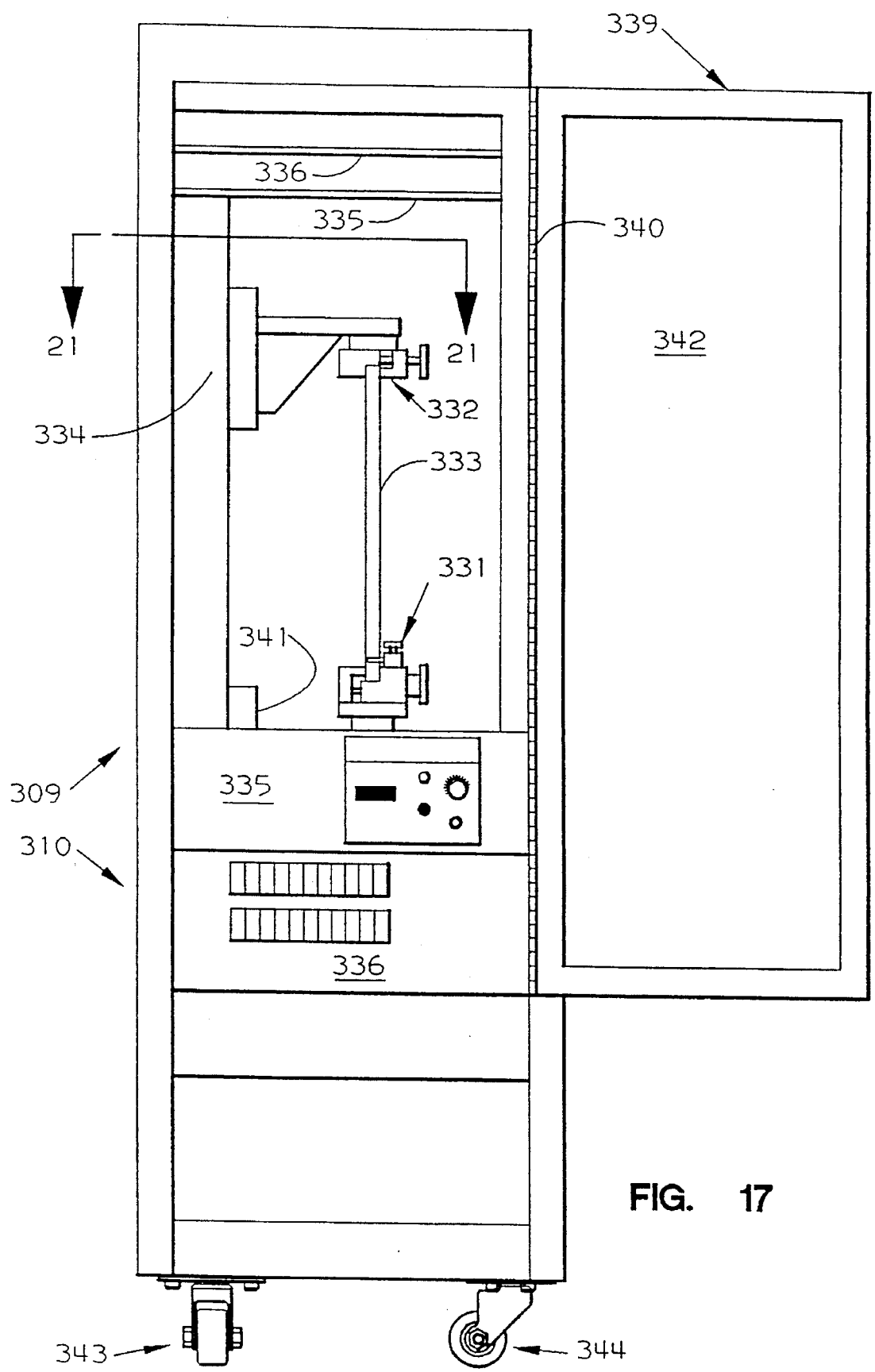
FIG. 17 illustrates one of the stations of the MDS tester of FIG. 15.

FIG. 17 schematically shows a typical station. The test section contains a rotatable lower card clamp 331 and a rotationally fixed upper card clamp 332 for positioning card 333 during torsion testing. The vertical position of the upper clamp is controlled by a linear positioning slide 334. Two stiffener plates 335, 336 minimize twisting of the machine. The lower section 310 is separated from the upper section 309 by a cowling that forms a horizontal bottom wall (not shown), a section 337 that slants toward the front and forms the operator's panel, and a section 338 vertically covering part of the bottom section that can be accessed by removing the cowl. A front door 339 with hinge 340, is opened for loading and unloading test cards. The machine includes an interlock 341 which prevents operation (twisting of the cards) when the door is opened. The door has a central section 342 of clear material (such as polycarbonate) through which testing may be safely observed. The test station is supported by casters 343, 344 for moving the tester, and the casters can be locked into position for stability.

Figure 18:
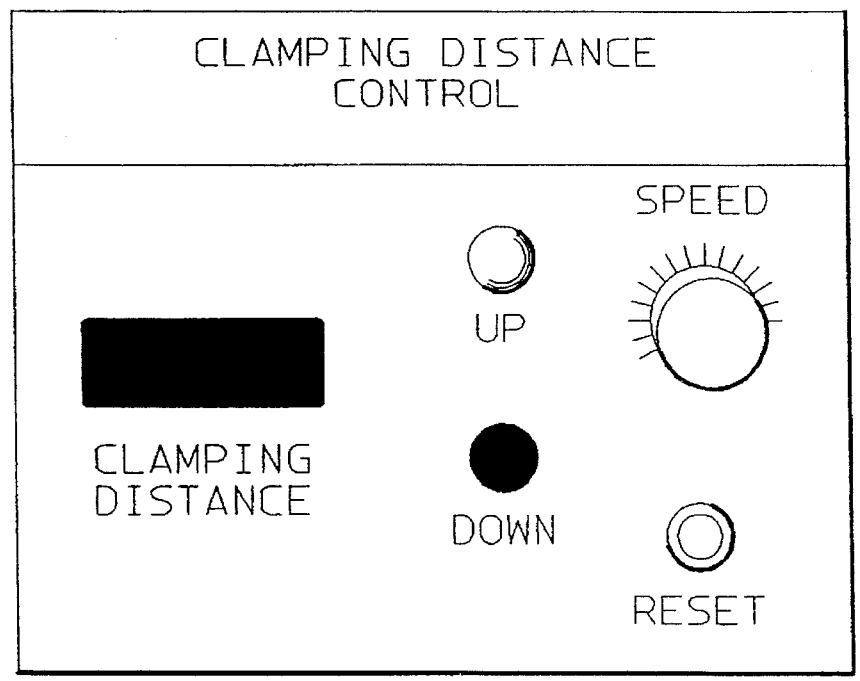
FIG. 18 shows a plan of the clamping distance control panel included in each station of the tester of FIG. 15.

FIG. 18 shows the clamping distance control section of the operator's panel of each test station. Momentary contact push buttons 351, 352 are for moving the upper clamp up and down respectively. Dial 353 controls the speed of the slide motor. A reset 354 is provided. The distance between the clamps is automatically determined as described below and displayed at 355.

Figure 19:
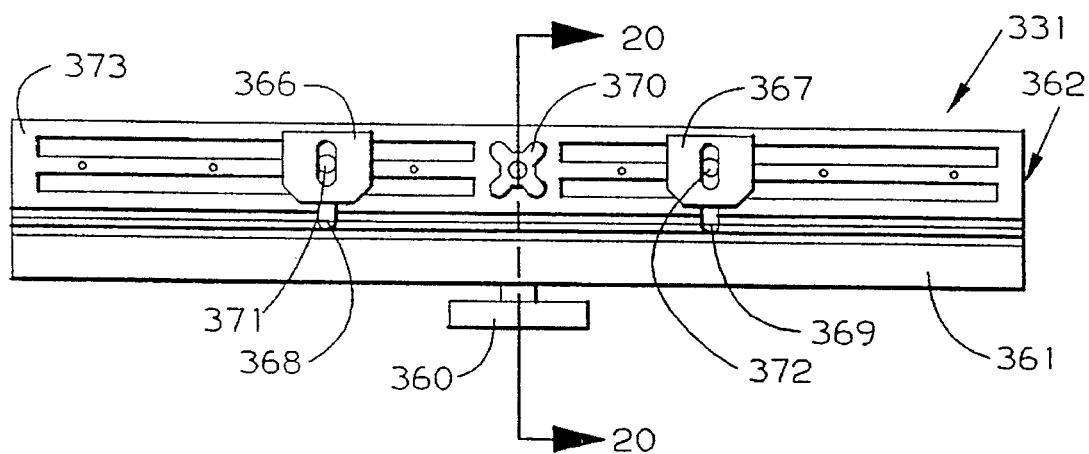
FIG. 19 shows a top view of the lower circuit board clamp of the tester of FIG. 15.
Figure 20:
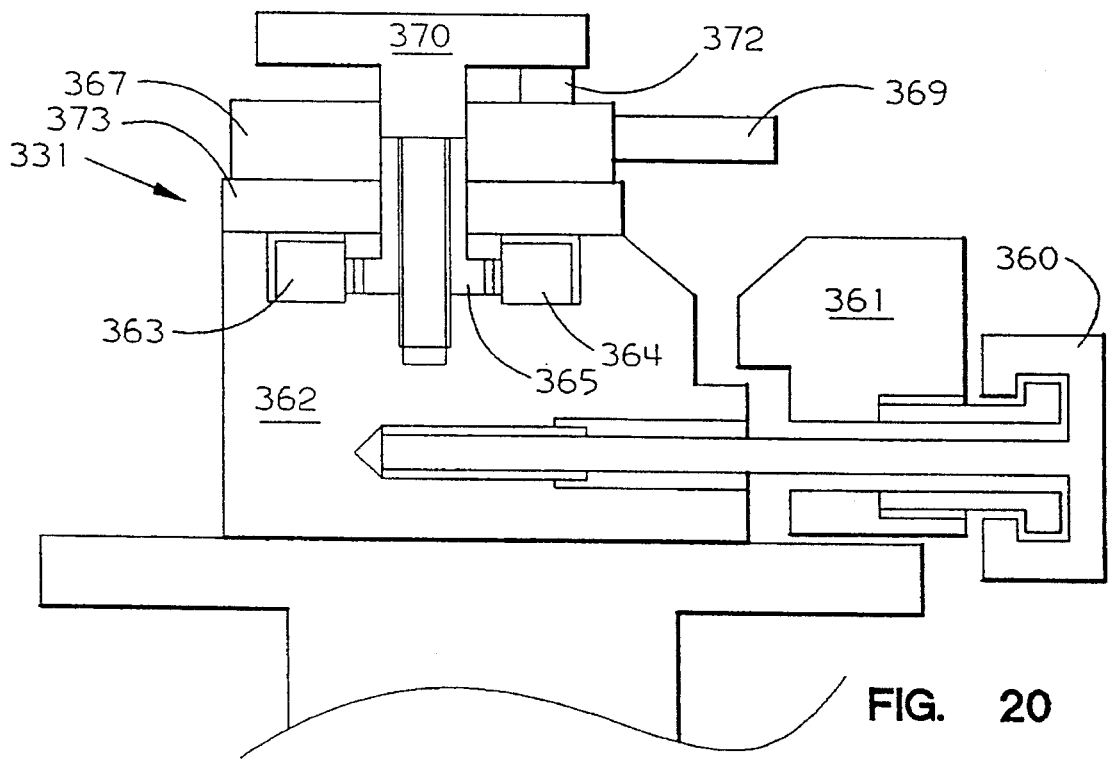
FIG. 20 is a partial sectional view taken through 20—20 of FIG. 19.

FIG. 19 is a top view of lower clamp 331. Clamp knob 360 moves grip 361 horizontally with respect to support 362 to clamp a circuit board (see FIG. 17). Two gear racks 363, 364 positioned in keyways, communicate with pinion gear 365 to move the racks in the longitudinal direction of the clamp, equally and in opposite directions in their respective keyways. Each gear rack is mechanically connected (not shown) to one of the centering slides 366, 367 to move the slides relatively closer or further apart in the longitudinal direction of the clamp. Thus, the distances between the longitudinal center of the clamp and end of the centering slides are always equal.

When a circuit board is loaded into the lower clamp the slides are moved together and the circuit board position is adjusted until both pins 368, 369 are against respective lateral edges of the circuit board. This assures that the circuit board is exactly centered in the lower clamp. Then lock knob 370 is turned to lock the pinion gear and hold the sliders in place. The circuit board can be removed pushing one of the buttons 371, 372 and sliding the board out in its lateral direction. If another board of the same size is loaded it is automatically centered simply by moving one of the pins back, sliding the board laterally into the clamp until board is against the other pin and releasing the pin so that the pins rest against the lateral edges of the board. Cover plate 373 holds the gear racks in the keyways and provides slots for supporting the centering slides and providing for the movement of the connection between each gear rack and its respective, connected centering slide as the centering slides move closer and further apart.

Figure 21:
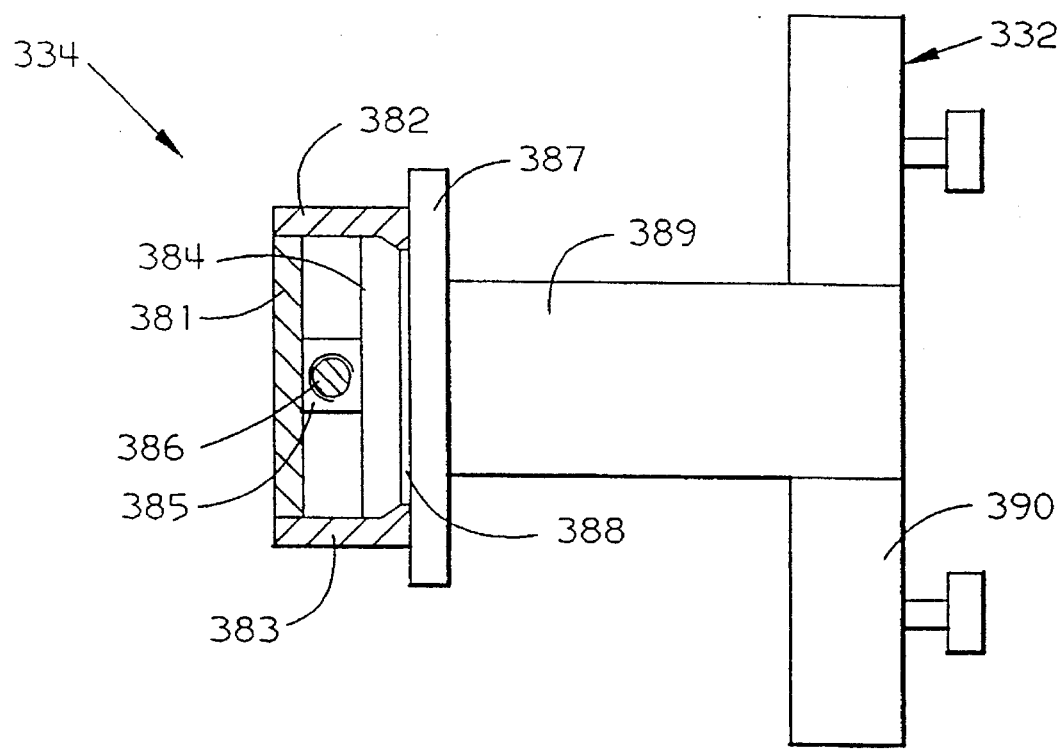
FIG. 21 is a partial section of the upper clamp, screw drive, and slide of the station of FIG. 17.

FIG. 21 is a top view of the upper clamp 332 with a partial section of slide 334. Slide 334 includes back plate 381, and side plates 382, 383. The upper clamp includes an inner sliding plate 384 connected to nut 385 which communicates with a jack screw 386 to selectively position the upper clamp in the vertical direction. The interior sliding plate communicates with an external sliding plate 387 which interact for sliding along slide 334. A spacer plate 388 separates the interior from the exterior sliding plates. The exterior sliding plate supports top support plate 389 which supports a top plate 390 of upper clamp 332.

Figure 22:
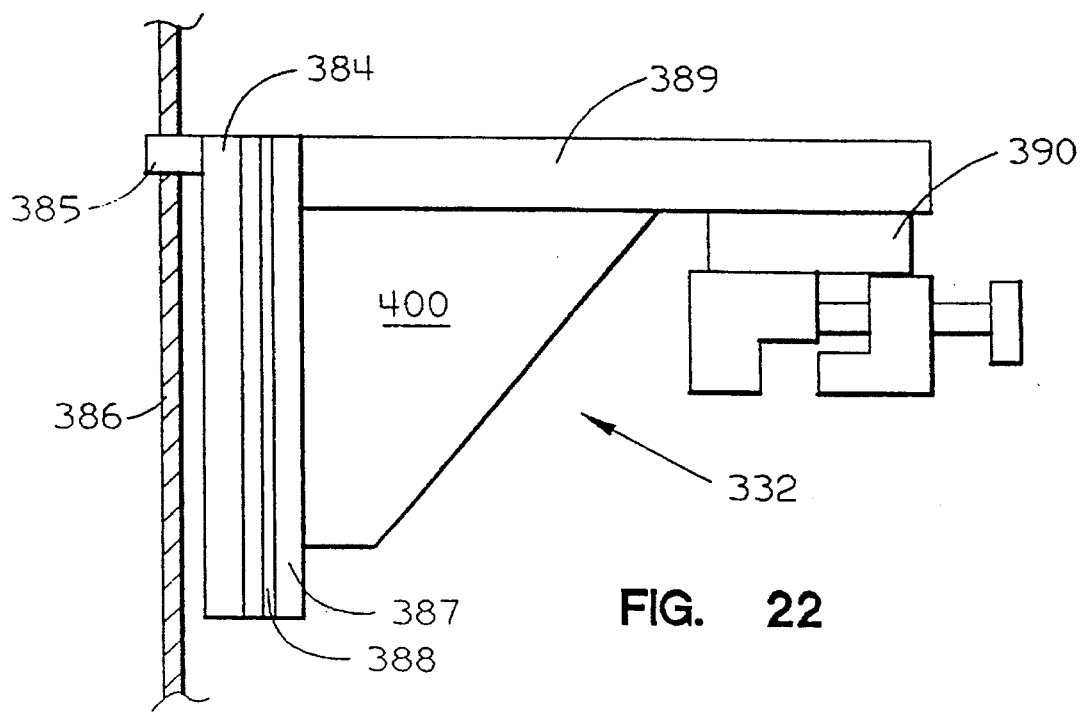
FIG. 22 is an elevation view of the upper clamp of FIG. 21 engaged with the screw drive.

FIG. 22 is a side view of upper clamp 332 with part of jack screw 386 shown. Stiffener plate 400 connects between top plate 389 and outer slide plate 387. Knob 401 moves slide jaw 402 closer/further from fixed jaw 403 to clamp a circuit board for testing.

Figure 23:
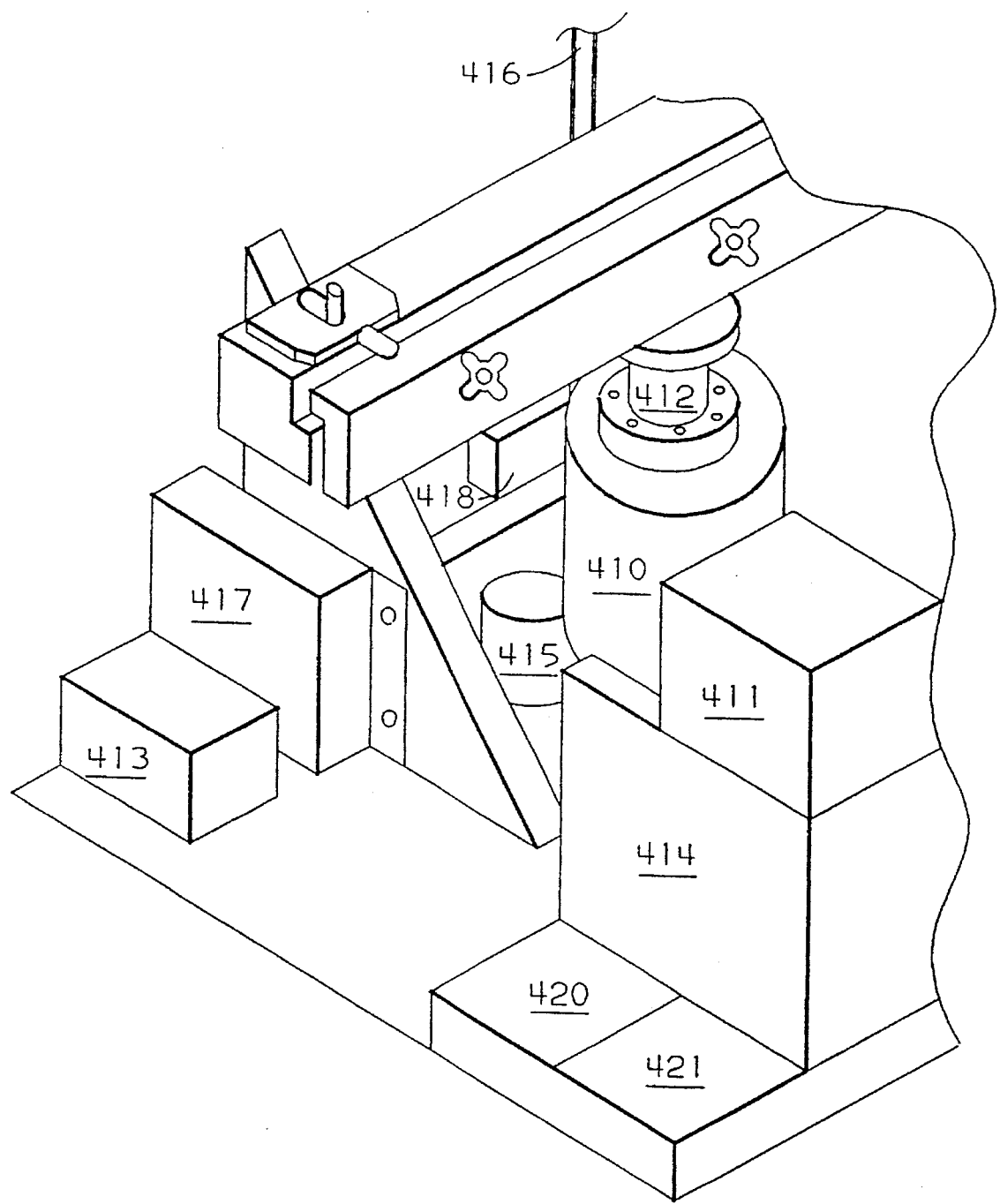
FIG. 23 is an isometric view of a part of the station of FIG. 17 including the lower clamp and drive motors, with the cowling removed.

FIG. 23 is a schematic isometric view of the part of the typical test station of FIG. 17 under the cowling. Servo motor 410 (such as Compumotor Dynaserve™ model DR 1060B (Dynaserve is a trademark of Parker Compumotor, Inc.) is rigidly mounted in the middle of the bottom section of each test station. Motor amplifier 411 regulates power to the motor and provides quadrature position feed back information signals. Torque transducer 412 measures the torque of the motor and is connected to torque signal unit 413 to provide a conditioned torque signal (both are provided by Sensor Development Corporation). 12 volt DC power supply 414 provides power for limit switches (not shown), ultrasonic distance sensor (not shown), and torque meter 412. The slide motor 415 is connected to turn slide jack screw 416 to control the vertical position of the upper clamp (see FIG. 21). Slide motor control box 417 regulates power for the slide motor. Ultrasonic sensor 418 (CONTAQ Technologies) measures the vertical position of the top clamp to determine the distance between the clamps for display on the operator's panel, and logging by the computer for each test. AC power is distributed by terminal blocks 420, 421.

Figure 24:
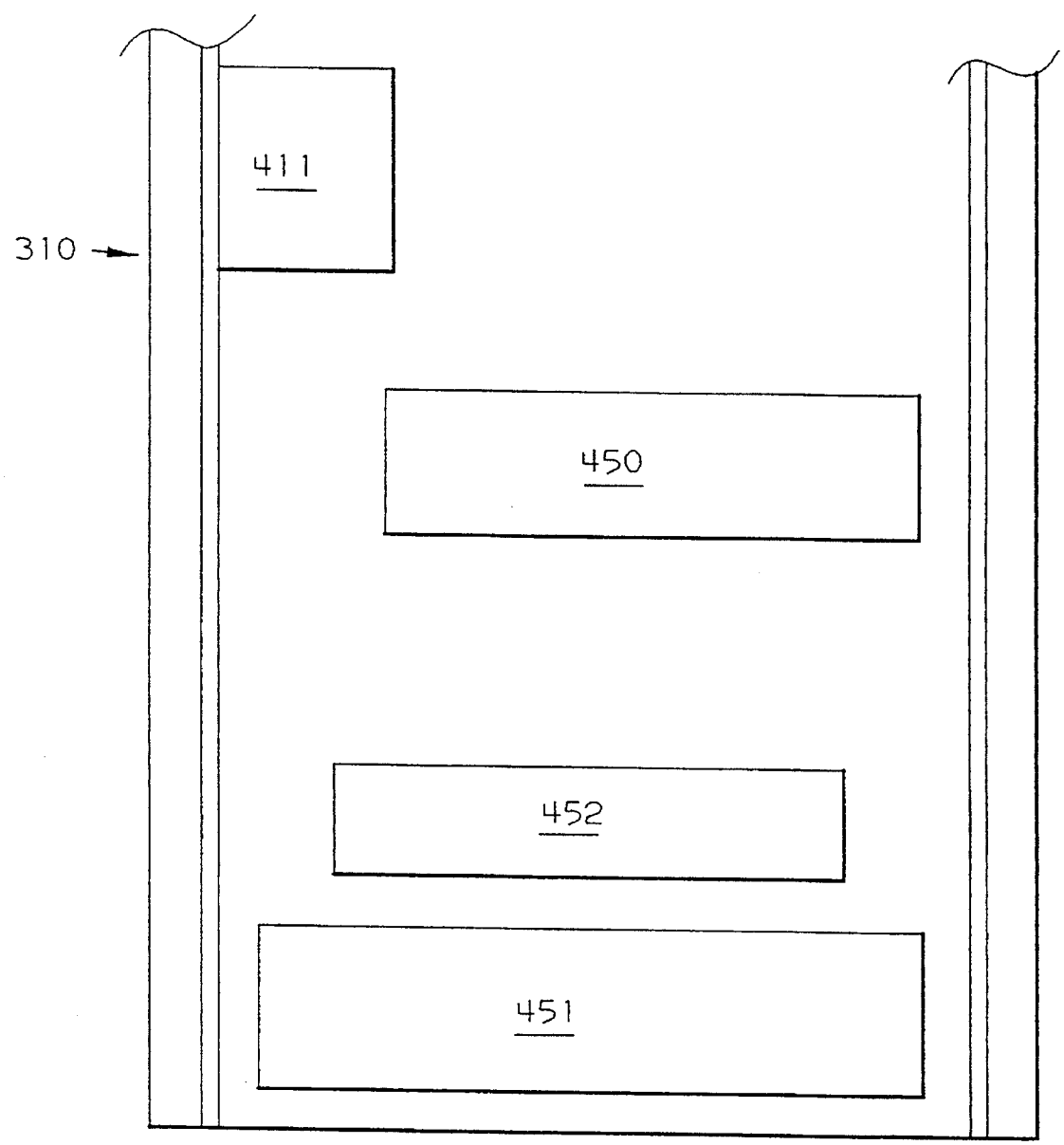
FIG. 24 is a rear view of the bottom section of the operator station of the tester of FIG. 15 with the back door removed.

FIG. 24 is a rear view of bottom section 310 of the main test station 304 with the back door (not shown) opened. The back end of drive motor amplifier 411 is seen at the top left of the drawing. Cable interface board connects the main station with any other stations in the machine. AC power box 451 provides for connection to AC power which is distributed to terminal blocks 420, 421 in FIG. 23. An AnaTech Test Circuit Monitor 452 is provided.

Although control of the machine and analysis could be provided purely by permanently configured hardware, it is convenient to provide a general purpose computer system which is configured during operation to provide the necessary apparatus to provide the required functions.

Figure 25:
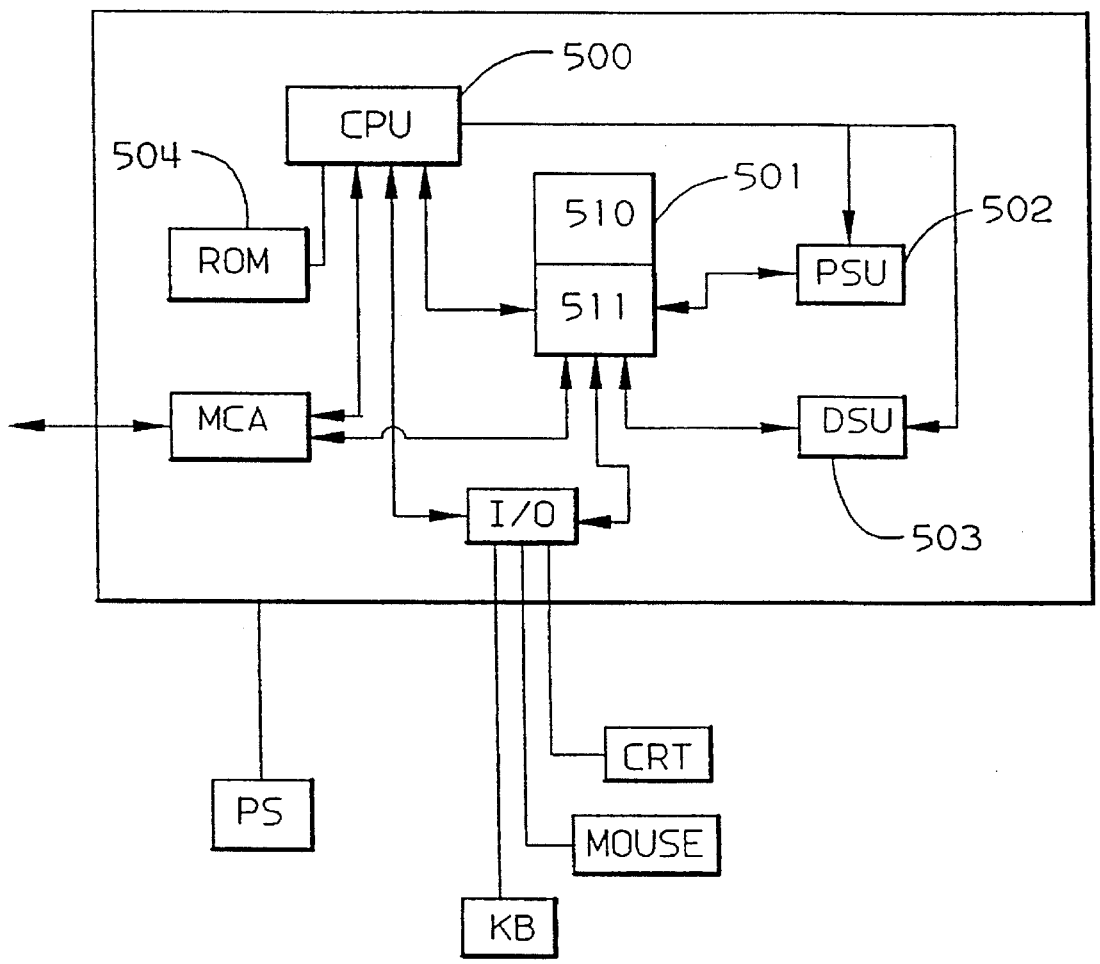
FIG. 25 is a schematic of the computer system of the operator station of the tester of FIG. 15.

As shown schematically in FIG. 25, the computer preferably includes a central processor unit (CPU) 500, random access memory (RAM) 501, a program storage unit (PSU) 502, a data storage unit (DSU) 503, and ROM 504 for initially transferring signals from the program storage unit to configure the RAM to proved various apparatus needed to control the CPU for controlling the machine during testing and analysis. The computer includes a motor control adapter (MCA) 505, such as an 8-axis Delta Tau PMAC-PC adapter, to control the various motors in the machine. The storage units include magnetic switches, optical switches, solid state switches or other machinery to cooperate with apparatus to generate signals to configure the RAM to provide apparatus required to control the CPU. The PSU and DSU storage devices can be combined if desired. During operation the RAM includes apparatus to present menus to the user and react to function keys, action bars, or mouse input (not shown). The RAM also includes control apparatus 510 to control the machine during testing and analysis apparatus 511 to perform the statistical analysis required of the system.

Although the invention has been described specifically in terms of preferred embodiments, such embodiments are provided only as examples. Those skilled in the art are expected to make numerous changes and substitutions including those discussed above, in arriving at their own embodiments without departing from the scope of the present invention and the following claims.

We claim:

1. A machine for testing circuit boards comprising:

fixturing means to hold two opposite edges of a circuit board along the length of each such edge;

motor means to rotate the fixturing means to twist the circuit board to induct cyclic torsion stress in the circuit board; and automatic control means to regulate the motor for providing predetermined torsion cycles.

2. The machine of claim 1 and further comprising means for automatically counting the number of torsion cycles and means for recording failure data including the location and the approximate torsion cycle at which failures occur.

3. The machine of claim 2, and further comprising automatic means for recording the torque and twist angle of every cycle, and in which the means for recording failure data include means to automatically record the exact cycle at which failures occur.

4. The machine of claim 1 and further comprising, means for precisely controlling the maximum angle of twist during each cycle to within at least 0.1 degree per inch of circuit board between the opposite edges.

5. The machine of claim 1 and further comprising means to precisely control the torque applied during each cycle sufficient to control twist angle to within 0.1 degree per inch of circuit board between clamps of the fixturing means at the opposite edges of the circuit board.

6. The machine of claim 5 further comprising means to precisely control the twist angle within 0.01 degrees per inch of circuit board along an axis of twisting.

7. The machine of claim 1 and further comprising, automatic means for measuring and automatic means for recording the maximum out-of-plane twist angle for each cycle.

8. The machine of claim 1 and further comprising, automatic means for measuring and automatic means for recording the maximum torque applied to the card during each cycle.

9. The machine of claim 1 and further comprising, means for adjusting the fixturing to accommodate various sized boards.

10. The machine of claim 1 and further comprising automatic means for centering edges of the circuit board in the fixturing means.

11. The machine of claim 1 and further comprising automatic means for measuring the distance between circuit board edge clamps of the fixturing means or the opposite edges of the circuit board.

12. The machine of claim 11 and further comprising means for automatically recording the measured distance.

13. The machine of claim 1 and further comprising means to automatically adjust the torque or angle of twist depending on the distance between circuit board edge clamps of the fixturing means or between the opposite edges of the circuit board.

14. The machine of claim 1 and further comprising means for automatically testing a series of boards using the same stored input of twist angle, torque frequency, or number of cycles to reduce reentering of data for each board.

15. The machine of claim 1 and said motor means is capable of providing at least 400 in-lbs.

16. The machine of claim 1 and further comprising means to limit the maximum clamping force applied by fixturing means at said opposite card edges.

17. A torque test machine, comprising:
   fixturing means including two circuit board clamps, for holding two opposite respective edges of a circuit board;
   means to adjust the spacing between the clamps for different circuit board sizes;
   a motor and gear box connected by a shaft to one of the clamps for rotating the clamp to cyclically twist the circuit board out-of-plane, for applying torsional stress cycles to the circuit board;
   measuring means for producing output signals for determining the distance between clamps, the torsion applied to the circuit board, or the angle of twist of the circuit board; control means to regulate power supplied to the motor to control the cycling and torsion or twist angle applied to the circuit board, depending on input control signals; and
   computer control interface means for receiving the control signals and transmitting the measured output signals to a computer.

18. The machine of claim 17 further including a personal computer system connected to the computer interface for controlling the test process, recording failure results, comparing results to results for previous tests, and analyzing the comparison to determine quality of the process.

19. The machine of claim 17 further including:
   automatic failure detection means connected to the circuit board for receiving output signals from the circuit board during the testing for detecting failures in electrical connections between components mounted on the circuit board and the circuits of the board during the torsional stressing of the board; and
   circuit board interface means to provide output signals to the computer control interface means for determining the torsion cycle of the detected failures of electrical connections.

20. An information handling system, comprising:
   means for storing the locations of failures of electrical interconnections between wiring of a circuit board and components mounted on the circuit board and a torsion cycle at which such failures occurred;
   means for storing a statistical data base derived from previous failures of similar circuit boards produced in one or more similar processes;
   means for comparing the locations and cycles of failures to the statistical data base; and
   means for analyzing the comparison to determine the quality of the process used to manufacture the circuit board.

21. A method for producing circuit boards comprising the steps:
   selecting one or more first circuit-boards which have been produced by a first production process;
   selecting one or more second circuit-boards with approximately the same structure as the first circuit board and which have been produced by a second production process which is similar to the first production process;
   exposing each of the selected circuit-boards to an equivalent set of out-of-plane torsion cycles until a multitude of circuit-board elements of each board have failed;
   detecting and recording the locations of failures of elements of the circuit boards;
   comparing the locations of failures of the first circuit boards with the locations of failures of the second circuit-boards;
   analyzing the comparison to identify differences in the quality of the production process; and
   producing circuit boards using the production process after the analysis.

22. The method of claim 21 in which the maximum angle of twist of each cycle is constant within 0.1 degrees per inch along the axis of twisting.

23. The method of claim 22 in which the maximum angle of twist of each cycle is constant within 0.01 degrees per inch along an axis of twisting.

24. The method of claim 21 and further comprising the step of, recording the approximate cycle for recorded failures and in which both the cycles of failures and the locations of failures are compared.

25. The method of claim 24 in which the set of torsion cycles include periodic pauses at small fractions of the total number of cycles, during which failures are detected discretely by visual inspection or probe testing.

26. The method of claim 24 in which failures are detected continuously by an automatic detection and recording system communicating with elements of the circuit-board.

27. The method of claim 21 and the first and second production process occurs on the same production line at different times.

28. The method of claim 27 and circuit-boards are periodically tested to maintain quality of the production line.

29. The method of claim 28 and the frequency of testing is selected to maintain a predetermined statistical level of quality.

30. The method of claim 28 in which the results of tests are included in a statistical data base to which the results of the tests are compared.

31. The method of claim 21 and one or more circuit boards produced in the first production process are exposed to thermal cycling fatigue tests sufficient to prove a desired level of quality of the first process.

32. The method of claim 21 in which elements of the circuit board include surface mounted modules and connections between the modules and circuit-board and during the comparison step, surface mount connection failures are sorted primarily by module and secondarily by location on the module.

33. The method of claim 21 in which multiple circuit-boards of the first process are tested to produce statistically valid fatigue data for comparison to the second process.

34. The method of claim 21 in which the selected circuit-boards are test vehicles that are different then normal production circuit boards and are passed through a production line for normal production circuit-boards.

35. The method of claim 21 in which the circuit boards are subject to the stress cycles until a multitude of electrical connections between components mounted on the circuit board and wiring patterns in the circuit board have failed.

36. The method of claim 21 in which the analysis of the failures considers the temperature cycle fatigue which is expected to be imposed on each element of customer shipped circuit boards.

37. A process for continuously manufacturing circuit boards, comprising the steps:

circuitizing circuit board substrates with circuit elements;

mounting components to the circuitized substrates with electrical connection elements;

selecting a board for testing during manufacturing;

exposing the selected test board to a set of out-of-plane torsion cycles until a population of multiple failures of connection elements has occurred;

detecting and recording failure data for the population of failures;

comparing the failure data to expected failure data; and determining the quality of the manufacturing process depending on the comparison.

38. A method of determining the reliability of circuit boards produced by a manufacturing process comprising the steps:

selecting a multitude of circuit boards produced by the process;

exposing the selected circuit boards to a set of out-of-plane torsion cycles until a population of multiple failures of circuit board elements have occurred in each circuit board;

detecting and recording failure data;

comparing failure data for the population of failures of each board to failure data for the population of failures for all the boards to determine consistency between the circuit boards; and statistically determining the reliability based on the comparison.

39. A method for manufacturing circuit boards, comprising the steps:

producing circuit boards by a manufacturing process;

selecting one or more first circuit boards produced by the manufacturing process;

exposing the circuit boards to a set of out-of-plane torsion cycles until a population of multiple failures of circuit board elements have occurred;

detecting and recording failure data for the first circuit boards;

changing one or more controllable parameters of the manufacturing process;

producing circuit boards after the change in parameters;

selecting one or more second circuit boards produced by the manufacturing process after such change of parameters;

detecting and recording failure data for the second circuit boards;

comparing the failure data for the population of failures for the first circuit boards to failure data for the population of failures of the second circuit boards; and determining whether the quality of the manufacturing process has improved, degraded or remained unchanged due to the changing of the process parameters depending on the comparison.

40. The method of claim 39 further comprising the step of producing circuit boards with the controllable parameters set depending upon the determination of quality.

* * * * *